United States Patent [19]
Urata et al.

[11] Patent Number: 6,133,495
[45] Date of Patent: *Oct. 17, 2000

[54] PROCESS FOR PRODUCING α-OLEFIN OLIGOMER

[75] Inventors: Hisao Urata; Takayuki Aoshima; Sugio Nishimura, all of Yokohama, Japan

[73] Assignee: Mitsubishi Chemical Corporation, Tokyo, Japan

[ * ] Notice: This patent is subject to a terminal disclaimer.

[21] Appl. No.: 08/952,746

[22] PCT Filed: Mar. 12, 1997

[86] PCT No.: PCT/JP97/00766

§ 371 Date: Jan. 2, 1998

§ 102(e) Date: Jan. 2, 1998

[87] PCT Pub. No.: WO97/33924

PCT Pub. Date: Sep. 18, 1997

[30] Foreign Application Priority Data

Mar. 14, 1996 [JP] Japan .................................. 8-085931
Mar. 15, 1996 [JP] Japan .................................. 8-087360

[51] Int. Cl.[7] .............................. C07C 2/24; C07C 2/08; C07D 207/00

[52] U.S. Cl. ........................... 585/513; 585/512; 585/527; 548/402; 548/564

[58] Field of Search .................................. 585/512, 513, 585/527; 548/402, 564

[56] References Cited

U.S. PATENT DOCUMENTS

| | | | |
|---|---|---|---|
| 5,376,612 | 12/1994 | Reagen et al. | 502/104 |
| 5,451,645 | 9/1995 | Reagen et al. | 526/97 |
| 5,523,507 | 6/1996 | Reagen et al. | 585/513 |
| 5,543,375 | 8/1996 | Lashier et al. | 502/117 |
| 5,563,312 | 10/1996 | Knudsen et al. | 585/513 |
| 5,910,619 | 6/1999 | Urata et al. | 585/513 |

FOREIGN PATENT DOCUMENTS 0 699 648 A1  3/1996  European Pat. Off. .
0 780 333 A1  6/1997  European Pat. Off. .

OTHER PUBLICATIONS

English abstract of Japanese Patent Application Laid–Open (Kokai) No. 8–325318 (No Date).
English abstract of Japanese Patent Application Laid–Open (Kokai) No. 8–333407 (No Date).
English abstract of GB 2,307,478 A (basic) relating to the corresponding Japanese Patent Application Laid–Open (Kokai) No. 9–143228 (No Date).
English abstract of Japanese Patent Application Laid–Open (Kokai) No. 8–3216 (No Date).
*Zeitschrift fuer Chemie* publication, 18(1), pp. 34–36 (1978).

*Primary Examiner*—Walter D. Griffin
*Attorney, Agent, or Firm*—Nixon & Vanderhye

[57] ABSTRACT

A process for producing an α-olefin oligomer, comprising subjecting an α-olefin to oligomerization in a reaction solution containing a chromium-based catalyst produced by bringing at least a chromium compound (a), a pyrrole ring-containing compound (b), an alkyl aluminum compound (c) and a halogen-containing compound (d) into contact with each other, wherein the chromium-based catalyst is a catalyst produced by bringing the pyrrole ring-containing compound (b), the alkyl aluminum compound (c) and the halogen-containing compound (d) into contact with each other in a hydrocarbon and/or halogenated hydrocarbon solvent, and then bringing the resultant mixed solution into contact with the chromium compound (a); or a catalyst produced by bringing the chromium compound (a), the pyrrole ring-containing compound (b), the alkyl aluminum compound (c) and the halogen-containing compound (d) into contact with each other in a hydrocarbon and/or halogenated hydrocarbon solvent in the absence of α-olefin under such a condition that the concentration of the chromium compound (a) is adjusted to not more than $8 \times 10^{-3}$ mol/liter. In accordance with the present invention, an α-olefin oligomer such as 1-hexene can be produced from α-olefin such as ethylene with a high yield and a high selectivity.

31 Claims, 1 Drawing Sheet

PROCESS FOR PRODUCING α-OLEFIN OLIGOMER

FIELD OF THE INVENTION

The present invention relates to a process for producing an α-olefin oligomer. More particularly, the present invention relates to a process for producing an α-olefin oligomer comprising mainly 1-hexene, from ethylene with a high yield and a high selectivity in an industrially useful manner.

BACKGROUND ART

It is hitherto known that an oligomerization of α-olefin such as ethylene is carried out in the presence of a chromium-based catalyst comprising a specific chromium compound and a specific organoaluminum compound in combination. For instance, in Japanese Patent Publication (KOKOKU) No. 43-18707, there is described a process for producing 1-hexene and polyethylene from ethylene by using a chromium-based catalyst comprising a compound of VIB-Group transition metal such as chromium and polyhydrocarbyl-aluminum-oxide.

Further, in Japanese Patent Application Laid-Open (KOKAI) No. 3-128904, there is described a method for the trimerization of an α-olefin by using a chromium-based catalyst obtained by reacting a chromium-containing compound having chromium-pyrrolyl bond with an alkyl metal or a Lewis acid. Furthermore, in South Africa Patent No. ZA93/0350, there is described a method for the trimerization of ethylene by using a chromium-based catalyst obtained by mixing a chromium compound, a pyrrole-containing compound, an alkyl metal and a halide source with each other in a common solvent.

On the other hand, the present inventors have previously proposed, in Japanese Patent Application Laid-Open (KOKAI) No. 6-145241, a method for the oligomerization of an α-olefin by using a chromium-based catalyst comprising a chromium-containing compound having chromium-pyrrole bond and alkyl aluminum in combination in such a manner that the chromium-containing compound and the alkyl metal compound are kept in non-contact with each other until these compounds are brought into contact with an α-olefin. According to the afore-mentioned method, 1-hexene can be produced by subjecting the α-olefin, particularly ethylene, to oligomerization in the presence of the catalyst having a high catalytic activity.

Further, the present inventors have also proposed, in Japanese Patent Application Laid-Open (KOKAI) No. 6-157655, a method for the oligomerization of an α-olefin in the presence of a chromium-containing compound produced by mixing a chromium compound with a pyrrole ring-containing compound in a hydrocarbon solvent, in which the contact between the chromium-containing compound and the alkyl aluminum compound is conducted in the same manner as described above. According to this method, 1-hexene having a high purity can be produced by subjecting an α-olefin, particularly ethylene, to trimerization in the presence of the catalyst having a high catalytic activity.

In addition, the present inventors have recently proposed, in Japanese Patent Application Laid-Open (KOKAI) No. 8-3216, a method of the oligomerization of an α-olefin by using a chromium catalyst comprising a chromium-containing compound, a pyrrole ring-containing compound, a alkyl metal compound and a halide source in combination, in such a manner that the chromium-containing compound and the alkyl metal compound are kept in non-contact with each other until these compounds are brought into contact with an α-olefin. According to this method, 1-hexene can be produced by subjecting the α-olefin, particularly ethylene, to oligomerization in the presence of the catalyst having a high catalytic activity.

However, in the method described in Japanese Patent Publication (KOKOKU) No. 43-18707, a large amount of polyethylene is produced simultaneously with the production of 1hexene. Whereas, in the case where the reaction condition is adjusted so as to reduce the amount of polyethylene as a by-product, there is caused such a problem that the catalytic activity of the catalyst is deteriorated. In the method described in Japanese Patent Application Laid-Open (KOKAI) No. 3-128904, there arises a problem in which although the amount of high-molecular weight polymer produced can be suppressed to a small level, the catalytic activity of the catalyst used is unsatisfactorily low.

In addition, in the method described in the South Africa Patent No. ZA93/0350, the catalytic activity of the catalyst used therein is still insufficient from a standpoint of conducting the oligomerization of α-olefin in an industrial-scale, though the method exhibits a high selectivity for 1-hexene. Further, in the method described in the Japanese Patent Application Laid-Open (KOKAI) Nos. 6-145241 and 6-157655, the catalytic activity of the catalyst used therein is also still insufficient from a standpoint of conducting the oligomerization of α-olefin in an industrial-scale. On the other hand, in the method described in the Japanese Patent Application Laid-Open (KOKAI) No. 8-3216, the selectivity for 1-hexene is insufficient, though the catalyst used in the method exhibits a sufficient catalytic activity to conduct the industrial-scale oligomerization of α-olefin.

The present invention aims at solving the afore-mentioned problems. An object of the present invention is to provide a process for producing an α-olefin oligomer such as 1-hexene with an extremely high yield and a high selectivity in an industrially advantageous manner.

DISCLOSURE OF THE INVENTION

As the results of the present inventors' earnest studies for accomplishing the above aim, it has been found that by using a specific chromium-based catalyst produced by a specific method, the oligomerization of an α-olefin, especially trimerization of ethylene, can be conducted in the presence of the catalyst having a high catalytic activity to produce 1-hexene having a high purity. The present invention has been attained on the basis of this finding.

In a first aspect of the present invention, there is provided a process for producing an α-olefin oligomer, comprising subjecting an α-olefin to oligomerization in the presence of a reaction solution containing a chromium-based catalyst prepared by bringing at least a chromium compound (a), a pyrrole ring-containing compound (b), an alkyl aluminum compound (c) and a halogen-containing compound (d) into contact with each other, wherein the chromium-based catalyst is prepared by bringing the pyrrole ring-containing compound (b), the alkyl aluminum compound (c) and the halogen-containing compound (d) into contact with each other in a hydrocarbon and/or halogenated hydrocarbon solvent, and then bringing the resultant mixed solution into contact with the chromium compound (a).

In addition, in a second aspect of the present invention, there is provided a process for producing an α-olefin oligomer comprising subjecting an α-olefin to oligomerization in the presence of a reaction solution containing a chromium-based catalyst prepared by bringing at least a chromium compound (a), a pyrrole ring-containing compound (b), an alkyl aluminum compound (c) and a halogen-containing compound (d) into contact with each other, wherein the chromium-based catalyst is prepared by bringing the chromium compound (a), the pyrrole ring-containing compound (b), the alkyl aluminum compound (c) and the halogen-containing compound (d) into contact with each other in the hydrocarbon and/or halogenated hydrocarbon solvent in the absence of the α-olefin under the condition that the concentration of the chromium compound (a) in the mixed solution is adjusted to not more than $8 \times 10^{-3}$ mol/liter.

The present invention is described in detail below.

In the process according to the present invention, a chromium-based catalyst produced by bringing at least a chromium compound (a), a pyrrole ring-containing compound (b), an alkyl aluminum compound (c) and a halogen-containing compound (d) into contact with each other, is used.

The chromium compounds (a) suitably used for the production of the chromium-based catalyst in the process of the present invention are represented by the general formula (1):

$$CrX_n \quad (1)$$

In the above general formula (1), a valence of chromium is 0 to 6; X may be same or different and represents an optional organic or inorganic group, or an anionic atom; and n is an integer of 1 to 6. It is preferred that n is an integer of not less than 2.

As the afore-mentioned organic groups, there can be used various organic groups having usually 1 to 30 carbon atoms. Specific examples of the suitable organic groups may include hydrocarbon groups, carbonyl groups, alkoxy groups, carboxyl groups, β-diketonate groups, β-keto-carboxyl groups, β-keto-ester groups, amide groups or the like. Examples of the hydrocarbon groups may include alkyl groups, cycloalkyl groups, aryl groups, alkylaryl groups, aralkyl groups, a cyclopentadienyl group or the like. Examples of the afore-mentioned inorganic groups may include chromium salt-forming groups such as a nitric group and a sulfuric group. Examples of the afore-mentioned anionic atoms may include oxygen, halogen or the like.

In addition, a complex comprising the afore-mentioned chromium compound and an electron donor is suitably used as the chromium compound. Such an electron donor may be selected from compounds containing nitrogen, oxygen, phosphorus or sulfur.

Examples of the nitrogen-containing compounds may include nitrile, amine, amide or the like. Specific examples of the nitrogen-containing compounds may include acetonitrile, pyridine, dimethyl-pyridine, dimethyl-formamide, N-methyl-formamide, aniline, nitrobenzene, tetramethyl-ethylene-diamine, diethylamine, isopropyl amine, hexamethyl disilazane, pyrrolidone or the like.

Examples of the oxygen-containing compounds may include esters, ethers, ketones, alcohols, aldehydes or the like. Specific examples of the oxygen-containing compounds may include ethyl acetate, methyl acetate, tetrahydrofuran, dioxane, diethyl ether, dimethoxy ethane, diethylene glycol dimethyl ether, triethylene glycol dimethyl ether, acetone, methyl ethyl ketone, methanol, ethanol, acetaldehyde or the like.

Examples of the phosphorus-containing compounds may include hexamethyl phosphoramide, hexamethyl phosphorous triamide, triethyl phosphite, tributyl-phosphine-oxide, triethyl phosphine or the like. Examples of the sulfur-containing compounds may include carbon disulfide, dimethyl sulfoxide, tetramethylene sulfone, thiophene, dimethyl sulfide or the like.

Accordingly, examples of the complexes comprising the chromium compound and the electron donor may include ether complexes of chromium halide, ester complexes of chromium halide, ketone complexes of chromium halide, aldehyde complexes of chromium halide, alcohol complexes of chromium halide, amine complexes of chromium halide, nitrile complexes of chromium halide, phosphine complexes of chromium halide, thioether complexes of chromium halide, or the like.

It is preferred that the chromium compound (a) is soluble in such hydrocarbon or halogenated hydrocarbon solvents as described hereinafter. Examples of such chromium compounds may include salts of chromium and β-diketonate, salts of chromium and carboxylic acid, salts of chromium and an anion derived from β-keto-esters, salts of chromium and β-keto-carboxylic acid, amide complexes of chromium, carbonyl complexes of chromium, carbene complexes of chromium, various cyclopentadienyl complexes of chromium, alkyl complexes of chromium, phenyl complexes of chromium or the like. Specific examples of these complexes may include chromium (III)-acetyl acetonate, chromium (III)-trifluoro-acetyl acetonate, chromium (III)-hexafluoro-acetyl acetonate, chromium (III) (2,2,6,6-tetramethyl-3,5-heptane-dionate), $Cr(PhCOCHCOPh)_3$ (wherein Ph represents a phenyl group), chromium (II) acetate, chromium (III) acetate, chromium (III)-2-ethyl hexanoate, chromium (III) benzoate, chromium (III) naphthenate, $Cr(CH_3COCHCOOCH_3)_3$, chromium (II)-bis-(trimethylsilyl)amide, $Cr(CO)_6$, $(C_6H_6)Cr(CO)_3$, $(CO)_5Cr(=CCH_3(OCH_3))$, $(CO)_5Cr(=CC_6H_5(OCH_3))$, $CpCrCl_2$ (wherein Cp represents a cyclopentadienyl group), $(Cp*CrClCH_3)_2$ (wherein Cp* represents a pentamethyl-cyclopentadienyl group), $(CH_3)_2CrCl$ or the like. Among them, especially preferred chromium compounds are salts of chromium and β-diketonate, salts of chromium and an anion derived from β-keto-esters, salts of chromium and carboxylic acid, salts of chromium and β-keto-carboxylic acid or the like. Incidentally, in the present invention, as the chromium compounds, any compounds containing a chromium atom may be used. Further, the chromium compounds may also contain any metal other than chromium.

The pyrrole ring-containing compound (b) used for the production of the chromium-based catalyst in the process of the present invention are substituted or unsubstituted pyrroles, or metal salts thereof, i.e., metal pyrrolide.

Examples of the afore-mentioned substituted pyrroles may include, in addition to 2,5-dimethyl-pyrrole, 3,4-dichloro-pyrrole, 2,3,4,5-tetrachloro-pyrrole, 2-formyl pyrrole, 2-acetyl pyrrole, 2,3,4-trimethyl pyrrole, 3,4-diethyl pyrrole, tetrahydro-indole, 3,3',4,4'-tetramethyl-2,2'-dipyrrolo-methane or the like.

As the metal contained in the afore-mentioned metal pyrrolide, there can be used any metal selected from 1-Group metals, 2-Group metals, 13-Group metals and 14-Group metals. Examples of the preferred metal pyrrolides may include lithium pyrrolide, sodium pyrrolide, potassium pyrrolide, cesium pyrrolide, magnesium dipyrrolide, diethyl aluminum pyrrolide, ethyl aluminum dipyrrolide, aluminum tripyrrolide, lithium-2,5-dimethyl pyrrolide, sodium-2,5-dimethyl pyrrolide, potassium-2,5-dimethyl pyrrolide, cesium-2,5-dimethyl pyrrolide, diethyl-aluminum-2,5-dimethyl pyrrolide, ethyl-aluminum-bis(2,5-dimethyl pyrrolide), trichloro-germanium pyrrolide or the like.

Further, as the preferred metal pyrrolides, there can also be exemplified lithium-3,4-dichloro-pyrrolide, sodium-2,3, 4,5-tetrachloro-pyrrolide, lithium-2,3,4-trimethyl pyrrolide, diethyl aluminum-2,3,4-trimethyl pyrrolide, sodium-3,4-diethyl pyrrolide, diethyl aluminum-3,4-diethyl pyrrolide or the like.

As the alkyl aluminum compounds (c) suitably used for the production of the chromium-based catalyst in the process of the present invention, there may be exemplified alkyl aluminum compounds represented by the following general formula (2):

$$R^1_m Al(OR^2)_n H_p X_q \qquad (2)$$

In the afore-mentioned general formula (2), $R^1$ and $R^2$ represent a hydrocarbon group having usually 1 to 15 carbon atoms, preferably 1 to 8 carbon atoms and may be same or different; X represents a halogen atom; m, n, p and q represent numbers satisfying the relationships of $0<m\leq 3$, $0\leq n<3$, $0\leq p<3$ and $0\leq q<3$, respectively, with the proviso that a sum of m, n, p and q is equal to 3.

Examples of the afore-mentioned alkyl aluminum compounds may include trialkyl aluminum compounds represented by the below-mentioned general formula (3), halogenated alkyl aluminum compounds represented by the below-mentioned general formula (4), alkoxy alkyl aluminum compounds represented by the below-mentioned general formula (5), hydrogenated alkyl aluminum compounds represented by the below-mentioned general formula (6), aluminoxanes represented by the below-mentioned general formula (7) or the like. In the below-mentioned respective general formulae, $R^1$, X and $R^2$ have the same meanings as defined above.

$$R^1_3 Al \qquad (3)$$

$$R^1_m AlX_{3-m} \qquad (4)$$

$(1.5 \leq m < 3)$

$$R^1_m Al(OR^2)_{3-m} \qquad (5)$$

$(0<m<3$, preferably $1.5 \leq m<3)$

$$R^1_m AlH_{3-m} \qquad (6)$$

$(0<m<3$, preferably $1.5 \leq m<3)$

$$R^1_2(AlO)(R^1AlO)_m AlR^1_2 \qquad (7)$$

$(0 \leq m \leq 30$, preferably $1 \leq m)$

Specific examples of the afore-mentioned alkyl aluminum compounds (c) may include trimethyl aluminum, triethyl aluminum, tri-isobutyl aluminum, diethyl aluminum monochloride, diethyl aluminum ethoxide, diethyl aluminum hydride, methyl aluminoxane, isobutyl aluminoxane or the like.

The afore-mentioned alkyl aluminum compounds (c) can be used in the form of a mixture of any two or more thereof. In addition, trialkyl aluminum compounds, especially triethyl aluminum, are preferable used because the use of reducing the amount of undesirable by-product polymer produced. Further, a mixture of the trialkyl aluminum compound and the halogenated alkyl aluminum compound (such as alkyl aluminum monochloride or alkyl aluminum dichloride) can also be preferably used.

The halogen-containing compounds (d) used for the production of the chromium-based catalyst in the process according to the present invention may be any compounds containing a halogen atom. Among them, such compounds containing an element selected from the group consisting of those belonging to the 3-, 4-, 5-, 6-(except for chromium), 13-, 14- and 15-Groups of the Periodic Table are preferably used. As the halogen atom, chlorine and bromine are preferable, and chlorine is especially preferable.

Specific examples of the halogen-containing compounds (d) may include scandium chloride, yttrium chloride, lanthanum chloride, titanium tetrachloride, zirconium tetrachloride, hafnium tetrachloride, boron trichloride, aluminum chloride, diethyl aluminum chloride, ethyl aluminum sesquichloride, ethyl aluminum dichloride, gallium chloride, carbon tetrachloride, chloroform, dichlorometahne, dichloroethane, tetrachloroethane, aryl chloride, trichloroacetone, hexachloro-acetone, hexachloro-cyclohexane, 1,3,5-trichloro-benzene, hexachloro-benzene, trityl chloride, silicon tetrachloride, trimethyl-chlorosilane, germanium tetrachloride, tin tetrachloride, tributyl tin chloride, dibutyl tin dichloride, phosphorus trichloride, antimony trichloride, trityl-hexachloro-antimonate, antimony pentachloride, bismuth trichloride, boron tribromide, aluminum tribromide, carbon tetrabromide, bromoform, bromobenzene, silicon tetrabromide, iodomethane, di-iodomethane, hexafluorobenzene, aluminum fluoride, molybdenum pentachloride, tungsten hexachloride or the like.

Among these halogen-containing compounds (d), the compounds having a large number of halogen atoms are preferred. Further, the compounds (d) soluble in a hydrocarbon solvent or a halogenated hydrocarbon solvent as described hereinafter are preferred. As the preferred halogen-containing compounds, there may be exemplified carbon tetrachloride, chloroform, dichloroethane, tetrachloroethane, trichloro-acetone, hexachloro-acetone, titanium tetrachloride, germanium tetrachloride, tin tetrachloride or the like. These halogen-containing compounds may be used in the form of a mixture of any two or more thereof.

In accordance with the present invention, as the hydrocarbon solvent or the halogenated hydrocarbon solvent used as a reaction solvent in the production of the chromium-based catalyst, there can be exemplified hydrocarbons or halogenated hydrocarbons having usually not more than 30 carbon atoms. Specific examples of the solvents may include aliphatic and alicyclic saturated hydrocarbons such as n-hexane, cyclohexane, n-heptane or n-octane, aliphatic and alicyclic unsaturated hydrocarbons such as 2-hexene, cyclohexene or cyclo-octene, aromatic hydrocarbons such as toluene, benzene or xylene, halogenated hydrocarbons such as carbon tetrachloride, chloroform, methylene chloride or chlorobenzene or dichlorobenzene, or the like. Furthermore, as will be noted from the below-mentioned first method for preparing the chromium-based catalyst used in the process of the present invention, α-olefins such as 1-hexene can also be used as the solvent.

Among these solvents, the aliphatic and alicyclic saturated hydrocarbons, the aromatic hydrocarbons and a mixture thereof are preferred. Specific examples of the preferred solvents may include cyclohexane, n-heptane, benzene, toluene and a mixture of any two or more thereof.

In addition, in the present invention, although the chromium-based catalyst may be supported on a carrier such as an inorganic oxide, the chromium-based catalyst is preferably used as it is without supporting it on the carrier. That is, in accordance with the present invention, the chromium-based catalyst can exhibit a high catalytic activity even though it is not supported on the carrier. Thus, in the case where the chromium-based catalyst is used without being supported on the carrier, complicated operations required for supporting the catalyst on the carrier can be omitted. Further, the problem of increasing a total amount of the catalyst (a sum of the carrier and the catalytically active components) due to the use of the carrier can be avoided.

In accordance with the present invention, the chromium-based catalyst used for the oligomerization of α-olefin can be produced by either one of the below-mentioned two methods.

The first method for the production of the chromium-based catalyst used in the process of the present invention comprises the steps of bringing the pyrrole ring-containing compound (b), the alkyl aluminum compound (c) and the halogen-containing compound (d) into contact with each other in the hydrocarbon and/or halogenated hydrocarbon solvent, and then bringing the resultant mixed solution into contact with the chromium compound (a) to produce the chromium-based catalyst.

By adopting the afore-mentioned first catalyst production method, there can be obtained advantages such as enhanced catalytic activity of the catalyst, extremely high selectivity for trimer and extremely high purity of the α-olefin oligomers produced. The reason why the chromium-based catalyst produced by such a catalyst production method can exhibit a high catalytic activity for the oligomerization of α-olefin is considered as follows, though it has not clearly been determined yet.

That is, the substrate required to produce the catalytically active species which can exhibit so high a catalytic activity to provide a high selectivity for the trimer, can be effectively produced by preliminarily reacting the pyrrole ring-containing compound (b), the halogen-containing compound (d) and the alkyl aluminum compound (c) with each other. Whereas, in the other contact methods except for the below-mentioned second method for the production of the chromium-based catalyst, side reactions such as the reaction of the chromium compound (a) with only the alkyl aluminum compound (c), is likely to proceed simultaneously with the afore-mentioned reaction, thereby producing extremely unstable alkyl chromium compound. The alkyl chromium compound produced by such a side reaction still undergoes decomposition and reduction reaction, so that there is caused the de-metallization of the catalyst which is unsuitable for the oligomerization of α-olefin. Accordingly, in order to effectively produce the catalytically active species, it is necessary to preliminarily reacting the pyrrole ring-containing compound (b), the halogen-containing compound (d) and the alkyl aluminum compound (c) with each other.

The method (contact method) for react the pyrrole ring-containing compound (b), the alkyl aluminum compound (c) and the halogen-containing compound (d) with each other is not particularly restricted. Any two of these compounds may be first reacted with each other, and then the obtained reaction product may be reacted with the remaining component. Alternatively, these three compounds can be reacted with each other at the same time.

Incidentally, the afore-mentioned production of the chromium-based catalyst may be carried out in the presence of α-olefin. However, it is preferred that the production of the chromium-based catalyst be conducted in the absence of α-olefin, because the selectivity for the oligomerization of α-olefin become higher.

In the afore-mentioned method, the catalytic activity of the chromium-based catalyst for the oligomerization of α-olefin is influenced by the concentration of the chromium compound (a) when a mixed solution comprising the pyrrole ring-containing compound (b), the halogen-containing compound (d) and the alkyl aluminum compound (c) is reacted with the chromium compound (a). That is, in general, it is preferred that the chromium concentration upon the reaction of the afore-mentioned mixed solution with the chromium compound (a) be maintained at a low level, because the low chromium concentration enables the production of a chromium-based catalyst having a high catalytic activity.

The concentration of the chromium compound (a) upon the reaction between the mixed solution and the chromium compound (a) is preferably $1 \times 10^{-7}$ to 1 mol/liter, more preferably $1 \times 10^{-5}$ to $3 \times 10^{-2}$ mol/liter.

The amount of the pyrrole ring-containing compound (b) present in the reaction system is usually not less than 0.001 mole, preferably 0.005 to 1,000 moles, more preferably 0.01 to 100 moles based on one mole of chromium atom.

The amount of the alkyl aluminum compound (c) present in the reaction system is usually not less than 50 millimoles based on one mole of a chromium atom. In order to further enhance the catalytic activity and the selectivity for the trimer, the amount of the alkyl aluminum compound (c) used is preferably not less than 0.1 mole based on one mole of a chromium atom. However, from economical viewpoint, it is preferred that the upper limit of the amount of the alkyl aluminum compound (c) is usually $10^4$ moles.

The amount of the halogen-containing compound (d) present in the reaction system is usually not less than 1 millimole, preferably not less than 50 millimoles based on one mole of chromium atom. The upper limit of the amount of the halogen-containing compound (d) used is not particularly restricted. For example, the chromium compound (a), the pyrrole ring-containing compound (b) and the alkyl aluminum compound (c) can be added to the halogenated hydrocarbon solvent to produce the catalyst.

Incidentally, in the present invention, the chromium-based catalyst can be produced at the oligomerization reaction zone by other method than the method in which the chromium-based catalyst which has been preliminarily produced can be supplied to the oligomerization reaction zone. That is, after the pyrrole ring-containing compound (b), the halogen-containing compound (d) and the alkyl aluminum compound (c) are preliminarily reacted with each other in the reaction zone, the reaction product is reacted with the chromium compound (a) in the same reaction zone to produce the chromium-based catalyst, in which zone the oligomerization of α-olefin can be successively conducted.

The second method for the production of the chromium-based catalyst used in the process according to the present invention, comprises the steps of bringing the chromium compound (a), the pyrrole ring-containing compound (b), the alkyl aluminum compound (c) and the halogen-containing compound (d) into contact with each other in the hydrocarbon and/or halogenated hydrocarbon solvent in the absence of α-olefin while controlling the concentration of the chromium compound (a) in the resultant mixed solution to not more than $8 \times 10^{-3}$ mole/liter to produce the chromium-based catalyst.

By adopting the afore-mentioned catalyst production method, there can be obtained advantages such as enhanced catalytic activity of the obtained catalyst, high selectivity for the trimer and extremely high purity of the α-olefin oligomer produced. When the chromium-based catalyst is produced in the presence of α-olefin, the resultant catalyst shows a low selectivity for the α-olefin oligomer. The reason why the catalyst produced by such a method can exhibit a high catalytic activity for the oligomerization of α-olefin is considered as follows though it is not clearly determined yet. That is, it is suggested that by controlling the concentration of the chromium compound (a) in the hydrocarbon and/or halogenated hydrocarbon solvent to not more than $8 \times 10^{-3}$ mole/liter, preferably from $1 \times 10^{31\ 3}$ to $8 \times 10^{-3}$ mole/liter, useful catalytically active species can be effectively produced and maintained.

The amounts of the pyrrole ring-containing compound (b), the alkyl aluminum compound (c) and the halogen-containing compound (d) present in the reaction system are the same as those mentioned above as to the first catalyst production method.

Meanwhile, in the case where the chromium-based catalyst is produced by adding the alkyl aluminum compound (c) to the reaction solution obtained by bringing the chromium compound (a), the pyrrole ring-containing compound (b) and the halogen-containing compound (d) (especially, inorganic halogen-containing compound) into contact with each other, it is preferred that the reaction product of the pyrrole ring-containing compound (b) and the halogen-containing compound (d) be produced in the form of a precipitate showing such a typical infrared absorption as described hereinafter, before the addition of the alkyl aluminum compound (c). In this case, the chromium compound (a) may co-exist in the reaction system from the beginning as mentioned above, or may be added to the reaction system after the precipitate is produced but before the alkyl aluminum compound (c) is added thereto.

The time required to produce the afore-mentioned precipitate is varied depending upon the reaction temperature and concentrations of the respective components. However, if the reaction temperature and the concentration of the respective components are kept in the afore-mentioned ranges, the time required for the production of the precipitate is generally about several minutes. Accordingly, the total reaction time required when the alkyl aluminum compound (c) is added to the mixed solution of the chromium compound (a), the pyrrole ring-containing compound (b) and the halogen-containing compound (d) is preferably not less than 3 minutes, more preferably not less than 7 minutes. Especially, in the case where an inorganic halogen-containing compound is used as the halogen-containing compound (d), the reaction of the pyrrole ring-containing compound (b) with the halogen-containing compound (d) can proceed rapidly. Therefore, such a method is advantageous from economical viewpoint.

The afore-mentioned second method for producing the chromium-based catalyst involves various production methods which are different in sequence of the addition of the respective catalytic components to the solvent from each other. The examples of the production methods involved in the second method are as follows.

(1) Method in which the alkyl aluminum compound (c) is added to the mixed solution of the chromium compound (a), the pyrrole ring-containing compound (b) and the halogen-containing compound (d);

(2) Method in which the chromium compound (a) is added to the mixed solution of the pyrrole ring-containing compound (b), the alkyl aluminum compound (c) and the halogen-containing compound (d); and (3) Method in which the mixed solution of the alkyl aluminum compound (c) and the halogen-containing compound (d) is added to the mixed solution of the chromium compound (a) and the pyrrole ring-containing compound (b).

In the afore-mentioned individual production methods, the sequence of the addition between the compound and the mixed solution or between the mixed solutions may be optional. For example, in the afore-mentioned production method (3), the mixed solution of the chromium compound (a) and the pyrrole ring-containing compound (b) may be added to the mixed solution of the alkyl aluminum compound (c) and the halogen-containing compound (d).

In the afore-mentioned production method, in the case where inorganic halogen-containing compound is used as the halogen-containing compound (d), it is important that the reaction product of the pyrrole ring-containing compound (b) and the halogen-containing compound (d) is produced in the form of a precipitate before the alkyl aluminum compound (c) is added to the mixed solution of the chromium compound (a), the pyrrole ring-containing compound (b) and the halogen-containing compound (d) as described above.

The afore-mentioned precipitate contains, as a main component, a novel pyrrole derivative represented by the following general formula (I):

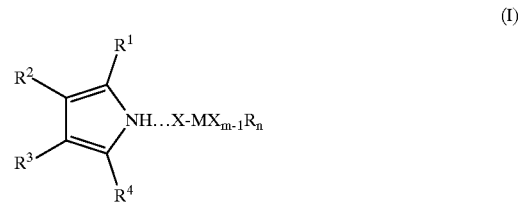

In the above general formula (I), $R^1$ to $R^4$ are a hydrogen atom or a linear or branched hydrocarbon group having 1 to 20 carbon atoms, in which $R^3$ and $R^4$ may integrally form a ring; X is a halogen atom; M is an element selected from the group consisting of those belonging to 3-Group, 4-Group, 6-Group (exclusive of chromium), 13-Group, 14-Group and 15-Group of the Periodic Table; m and n are numbers satisfying the relationships of $1 \leq n \leq 6$, $0 \leq n \leq 5$ and $2 \leq m+n \leq 6$ with the proviso that the sum of m and n is identical to the valence of the element M; n represents the number of Rs; R is a hydrogen atom or a linear or branched hydrocarbon group having 1 to 20 carbon atoms and when n is not less than 2, Rs may be the same or different.

As the afore-mentioned hydrocarbon groups, there can be exemplified a methyl group, an ethyl group, a propyl group, a butyl group or the like. As the afore-mentioned halogen atoms, there can be exemplified F, Cl, Br or the like. As the afore-mentioned elements, there can be exemplified Sc, Y, Ti, Zr, Hf, Mo, W, B, Al, Ga, In, Tl, Si, Ge, Sn, Pb, P, As, Sb or the like.

FIG. 1 shows an infrared absorption spectrum of the pyrrole derivative according to the present invention, which was obtained in Example 6 described hereinafter. As is apparently shown in FIG. 1, the pyrrole derivative is characterized by broad infrared absorption which is typically caused at a wavelength of 3100 to 3300 $cm^{-1}$ due to stretching vibration of the hydrogen-bonded NH.

The chromium-based catalyst produced by preparing the reaction product of the pyrrole ring-containing compound (b) and the halogen-containing compound (d) in the form of a precipitate before the addition of the alkyl aluminum compound (c), has a high catalytic activity for the oligomerization of α-olefin. The reason therefor is suggested as follows though it is not clearly determined yet.

That is, when the pyrrole ring-containing compound (b) and the halogen-containing compound (d) are sufficiently reacted with each other, the substrate which is essential to the production of catalytic active species exhibiting such a high catalytic activity so as to produce the α-olefin trimer with a high selectivity, can be obtained. In the case where the alkyl aluminum compound (c) is added to the mixed solution of the chromium compound (a), the pyrrole ring-containing compound (b) and the halogen-containing compound (d), unless the reaction has been preliminarily conducted to a sufficient extent, the chromium compound (a) is reacted with both unreacted pyrrole ring-containing compound (b) and alkyl aluminum compound at the same time when the chromium compound (a) is contacted with the alkyl aluminum compound (c), thereby producing extremely unstable alkyl chromium compound.

The alkyl chromium compound thus produced through the afore-mentioned reaction further undergoes the decomposition and reduction reaction in the absence of α-olefin as described in Japanese Patent Application Laid-Open (KOKAI) No. 6-145241, thereby causing the de-metallization of the catalyst which is unsuitable for the oligomerization of α-olefin. Therefore, in the case where the alkyl aluminum compound (c) is added to the mixed solution of the chromium compound (a), the pyrrole ring-containing compound (b) and the halogen-containing compound (d), in order to effectively produce the catalytically active species, it is required that the reaction product of the pyrrole ring-containing compound (b) and the halogen-containing compound (d) is produced in the form of a precipitate before the addition of the alkyl aluminum compound (c).

Among the afore-mentioned production methods (1) to (3), the method (2) in which the chromium compound (a) is added to the mixed solution of the pyrrole ring-containing compound (b), the alkyl aluminum compound (c) and the halogen-containing compound (d), is more preferable. The production method (2) has mainly the following advantages. That is, the obtained chromium-based catalyst can exhibit a high catalytic activity for the oligomerization of α-olefin, and the reaction of the pyrrole ring-containing compound with the halogen-containing compound can be accelerated by the co-existence of the alkyl aluminum compound irrespective of the kinds of halogen-containing compounds used.

In accordance with the present invention, in any of the afore-mentioned first and second methods, it is preferred that the reaction is conducted in the absence of an oxygen atom and/or water. The temperature used for the production of the catalyst can be optionally selected, but the temperature is preferably 0 to 150° C. The time required for the production of the catalyst (mixing time) is not particularly restricted, but is usually 0.1 minute to 48 hours, preferably 5 minutes to 3 hours.

After completion of the reaction for the production of the catalyst, the solvent is distilled off the reaction mixture to isolate the chromium-based catalyst. The distillation of the reaction solvent can be carried out by any known methods, i.e., by a method in which the reaction mixture is maintained at a higher temperature than the boiling point of the solvent or at normal temperature under a reduced pressure, or by a method in which an inert gas is caused to pass through the reaction mixture. However, in the process according to the present invention, the catalyst solution or suspension obtained without isolating the chromium-based catalyst from the solvent may also be used as the chromium-based catalyst as it is.

In the present invention, when the catalyst produced by the afore-mentioned method should be stored for a long period of time before it is used for the oligomerization of α-olefin, the catalyst may be preserved by immersing in an ordinarily used organic solvent. In this case, it is preferred that unsaturated hydrocarbon is contained in the organic solvent, because the inclusion of such an unsaturated hydrocarbon permits the catalyst to be kept more stable. It is more preferred that the catalyst is stored in the absence of oxygen and water.

As the unsaturated hydrocarbons to be contained in the organic solvent, there can be usually used those having not more than 30 carbon atoms. Examples of the suitable unsaturated hydrocarbons may include aliphatic or alicyclic unsaturated hydrocarbons such as ethylene, propylene, butene, pentene, hexene, heptene, octene, decene, cyclohexene or cyclooctene, aromatic hydrocarbons such as benzene, toluene, cumene, xylene or mesitylene, or the like. Among them, especially preferred unsaturated hydrocarbons are ethylene, butene, hexene, octene, decene, cyclohexene, benzene, toluene, xylene or a mixture of any two or more thereof.

The reason why the catalyst can be kept stable by the co-existence of the unsaturated hydrocarbon, is considered such that the unsaturated hydrocarbon can be coordinated to the metal of the coordinatively unsaturated catalyst which is an unsuitable complex, thereby causing the catalyst to be stabilized.

In the process according to the present invention, the temperature used for storing the catalyst is usually not more then 150° C., preferably from −78° C. to 150° C. In general, the lower the storing temperature the longer the period for which the catalyst can be stably preserved becomes. Specifically, the temperature used for storing the catalyst may be determined depending upon the intended storage period and the kinds of co-existing unsaturated hydrocarbons. Generally, as the co-existing unsaturated hydrocarbons, aromatic hydrocarbons are superior to aliphatic unsaturated hydrocarbons because the store containing aromatic hydrocarbons can withstand a higher temperature than the store containing aliphatic unsaturated hydrocarbons. In this sense, it is preferred that $C_6$ to $C_{12}$ aromatic hydrocarbons co-exists in the organic solvent.

In accordance with the present invention, the thus-stored catalyst can exhibit a sufficient catalytic activity for the oligomerization of α-olefin even after stored for at least 24 hours, usually for at least 36 hours.

Incidentally, since the unsaturated hydrocarbon coordinated to the catalyst for stabilization thereof is likely to be dissociated, it is preferable that the quantity and concentration of the unsaturated hydrocarbon existing around the catalyst is enhanced to inhibit the dissociation. From this standpoint, the concentration of the unsaturated hydrocarbon in the solvent used for the preservation of the catalyst is preferably not less than 5% by weight. Further, the unsaturated hydrocarbon is present in an amount of not less than 50 moles based on one mole of chromium atom. The molar amount of the unsaturated hydrocarbon per mole of chromium atom is preferably not less than 100 moles, more preferably not less than 1,000 moles.

In accordance with the present invention, the more preferable method for storing the catalyst is a method of adding the chromium compound, the pyrrole compound, the alkyl aluminum compound and the halogen-containing compound to the solvent containing the unsaturated hydrocarbon to prepare a solution into which the catalyst is dissolved, and storing the solution as it is. Since the catalyst can be rapidly produced, it can be considered that the production of the catalyst is completed at the time at which all the components are completely mixed together. Further, after the catalyst is produced in a solvent such as cyclohexane, the unsaturated hydrocarbon can be added to the reaction solution containing the resultant catalyst to preserve the catalyst. Furthermore, after the catalyst is produced in an appropriate solvent, the solvent may be distilled off to concentrate or isolate the catalyst and then the resultant catalyst may be dissolved in a solvent containing the unsaturated hydrocarbon to preserve the catalyst. Incidentally, since the catalyst isolated from the solution is likely to lose its catalytic activity, it is preferred that the isolated catalyst is rapidly dissolved in another solvent.

The catalyst stored in the solvent containing the unsaturated hydrocarbon according to the afore-mentioned method can be used as it is for the oligomerization of α-olefin. Alternatively, the concentrated or isolated catalyst by distilling the solvent from the reaction solution can also be used for the oligomerization of α-olefin.

In accordance with the present invention, the oligomerization of α-olefin can be conducted by ordinary methods. As the α-olefins as a raw material, there can be used linear or branched α-olefins having 2 to 30 carbon atoms. Specific examples of the α-olefins may include ethylene, propylene, 1-butene, 1-hexene, 1-octene, 3-methyl-1-butene, 4-methyl-1-pentene or the like. Among them, ethylene is especially preferable. When ethylene is used as the α-olefin, it is possible to produce 1-hexene as a trimer of ethylene with a high yield and a high selectivity.

As the solvent for the oligomerization of α-olefin, there can be used aliphatic or alicyclic saturated hydrocarbon having 4 to 20 carbon atoms, such as butane, pentane, hexane, heptane, cyclohexane, octane, methyl cyclohexane or decalin; aromatic hydrocarbons such as benzene, toluene, xylene, mesitylene or tetralin; aliphatic halogenated hydrocarbons such as chloroform, carbon tetrachloride, dichloromethane or dichloroethane; or the like. These solvents can be used singly or in the form of a mixture of any two or more thereof.

Also, as the solvent for the oligomerization of α-olefin, there can be used the α-olefins themselves as the reaction raw materials and other α-olefins than those used as the reaction raw materials. As the α-olefins used as the solvent, α-olefins having 4 to 30 carbon atoms are preferable, and α-olefins which can be maintained in a liquid state at normal temperature are especially preferable.

Among the afore-mentioned solvents, especially preferred solvents are the aliphatic saturated hydrocarbons or alicyclic saturated hydrocarbons having 4 to 7 carbon atoms, such as butane, pentane, hexane, heptane or cyclohexane. When these solvent are used, there can be obtained such an advantage that the catalyst can show a high catalytic activity and a high selectivity.

The amount of the chromium-based catalyst used in the oligomerization of α-olefin according to the present invention is usually $1 \times 10^{-7}$ to 0.5 mole (calculated as the amount of chromium atom contained in one liter of the solvent), preferably $1 \times 10^{-6}$ to 0.2 mole, more preferably $1 \times 10^{-5}$ to 0.05 mole. The reaction temperature used for the oligomerization of α-olefin, is usually 0 to 250° C., preferably 0 to 200° C. In addition, the reaction pressure used therefor may be selected from the range of normal pressure to 250 kg/cm², but the pressure of 100 kg/cm² is usually sufficient for the purpose. The reaction time used for the oligomerization of α-olefin, is usually 1 minute to 20 hours, preferably 0.5 to 6 hours.

Meanwhile, it is preferred that hydrogen is permitted to co-exist in the reaction system for the oligomerization of α-olefin, because properties of the polymer as a by-product can be improved by the co-existence of hydrogen. The amount of the co-existing hydrogen is usually 0.1 to 100 kg/cm² (calculated as a hydrogen partial pressure), preferably 1.0 to 80 kg/cm².

In the process according to the present invention, using the chromium-based catalyst produced by the afore-mentioned catalyst production method, the oligomerization of α-olefin can be conducted by a semi-batch method or by a continuous method.

In the semi-batch method, in general, α-olefin is continuously supplied into a reactor and reacted under a constant pressure. On the other hand, in the continuous method, there can be used a tubular reactor or a multi-stage mixing tank. The tubular reactor is basically a reactor of such a type in which reactants are introduced into one end of a linear tube pipe, or a coil-shaped or U-shaped curved tube pipe and the reaction product is discharged from the other end thereof. On the other hand, the multi-stage mixing tank is basically a reactor of such a type in which reactants are introduced into the first vessel of a plurality of vessels connected in series with each other and transported sequentially from one vessel to the subsequent vessel, and the reaction product is discharged from the final vessel of the multi-stage mixing tank.

In the process according to the present invention, the additional amount of the halogen-containing compound (d) can be supplied into the reaction zone during the oligomerization of α-olefin. Also, it is preferred that in addition to the halogen-containing compound, the additional amounts of the pyrrole ring-containing (b) or the alkyl aluminum compound (c) are supplied into the reaction zone. It is especially preferred that the additional amounts of both the halogen-containing compound (d) and the alkyl aluminum compound (c) are supplied into the reaction zone. As an example of the manners of supplying the additional amount of the halogen-containing compound (d) into the reaction zone, there can be used a method in which the additional amount of the halogen-containing compound is supplied together with the chromium-based catalyst produced. For example, the catalyst solution containing a large amount of liberated halogenated hydrocarbon, which is obtained when the chromium-based catalyst is produced in a halogenated hydrocarbon solvent, can be additionally supplied into the reaction zone. As the halogen-containing compound (d), the pyrrole ring-containing compound (b) and the alkyl aluminum compound (c) additionally supplied into the reaction zone, there can be generally used the same compounds as used for the production of the catalyst. However, if required, other compounds can also be used as the compounds to be additionally supplied. Examples of the preferred halogen-containing compounds (d) additionally supplied into the reaction zone may include halogenated hydrocarbons such as carbon tetrachloride or hexachloroethane, or compounds containing a halogen atom, especially a chlorine atom, bonded to an element belonging to 13-Group or 14-Group of the Periodic Table, such as ethyl aluminum dichloride, diethyl aluminum chloride or tin tetrachloride.

In the process according to the present invention, by additionally supplying the halogen-containing compound (d), especially both the halogen-containing compound (d) and the alkyl aluminum compound (c), into the oligomerization reaction zone, the catalyst present in the reaction zone can be activated, resulting in considerable increase in catalytic efficiency thereof. That is, although the catalytic activity of the catalyst being subjected to the reaction is deteriorated with the elapse of time, if the halogen-containing compound (d) is supplied thereto, the catalyst can be activated again so that the catalytic activity thereof is increased. Besides, the effect of activating the catalyst by the addition of the halogen-containing compound (d) can be exhibited not merely one time but repeatedly every time at which deterioration in catalytic activity of the catalyst is caused. Accordingly, the additional amount of halogen-containing compound (d) is preferably supplied to the reaction zone at the time at which the catalytic activity of the catalyst begins to be deteriorated or at the stage during which the deterioration in catalytic activity of the catalyst proceeds. Even when the halogen-containing compound (d) is added to the catalyst whose catalytic activity has been already deteriorated, the catalyst can be activated again. However, this is disadvantageous from the standpoint of productivility. The catalytic activity of the chromium-based catalyst used in the process according to the present invention begins to be deteriorated at the earliest about 5 minutes, usually about 15 minutes after the catalyst is subjected to the reaction. In many cases, subsequent to the time at which the catalytic activity of the catalyst begins to be deteriorated, the deterioration thereof proceeds continuously for 70 to 80 minutes. Accordingly, the additional amount of the halogen-containing compound (d) is supplied to the reaction zone where such a catalyst subjected to the reaction for not less than 5 minutes, especially for not less than 15 minutes is present. The supply of the additional amount of the halogen-containing compound (d) may be conducted only one time, or may be repeated several times at which the deterioration in catalytic activity of the catalyst occurs. The amount of the halogen-containing compound (d) to be additionally supplied each time, is preferably 0.1 to 200 moles, more preferably 1 to 100 moles based on one mole of chromium atom to be activated. Similarly, the amount of the pyrrole ring-containing compound (b) to be additionally supplied each time, is preferably 0.1 to 100 moles, more preferably 1 to 50 moles based on one mole of chromium atom to be activated. Further, the amount of the alkyl aluminum compound (c) to be additionally supplied each time, is preferably 1 to 1,000 moles, more preferably 5 to 500 moles based on one mole of chromium atom to be activated.

Accordingly, when the process according to the present invention is conducted in a semi-batch manner, the additional amount of the halogen-containing compound (d) may be supplied to the reaction zone at the stage at which not less than 5 minutes have elapsed after initiation of the reaction and the rate of consumption of α-olefin begins to be lowered. By supplying the additional amount of the halogen-containing compound (d) to the reaction zone one time or repeatedly several times, the amount of the α-olefin oligomer produced per unit weight of the chromium-based catalyst can be increased.

In addition, in the case where the process according to the present invention is conducted in a continuous manner using the tubular reactor, the tubular reactor is supplied at a tip end thereof with the solvent, the chromium-based catalyst, α-olefin or the like, and the halogen-containing compound (d) is additionally supplied into the reactor at its intermediate position where residence time of the catalyst is not less than 5 minutes. In this case, the halogen-containing compound (d) may be further supplied into the pipe reactor at several positions on the downstream side thereof.

In the case where the process according to the present invention is conducted using the multi-stage mixing tank, the solvent, the chromium-based catalyst and α-olefin are supplied to the first vessel thereof, and the halogen-containing compound (d) may be supplied to the second or subsequent vessel where the residence time of the catalyst is not less than 5 minutes. Similarly, in this case, the additional amount of the halogen-containing compound (d) can also be supplied to optional vessels subsequent to the vessel where the first supply of the halogen-containing compound (d) is carried out.

After completion of the oligomerization of α-olefin which is conducted according to the afore-mentioned method, polymer as a by-product is first removed form the resultant reaction solution, thereby enabling a solution containing α-olefin oligomer as a main reaction product to be recovered.

The removal or separation of the polymer as a by-product from the reaction solution can be appropriately conducted by using known solid-liquid separators. The α-olefin oligomer recovered may be subjected to purification treatment, if required. As the purification treatment of the α-olefin oligomer, there can be usually used a distillation method by which the aimed components can be recovered with a high purity. In accordance with the present invention, especially, 1-hexene having a high purity can be produced from ethylene in an industrially useful manner.

BEST MODE FOR CARRYING OUT THE INVENTION

Figure 1:
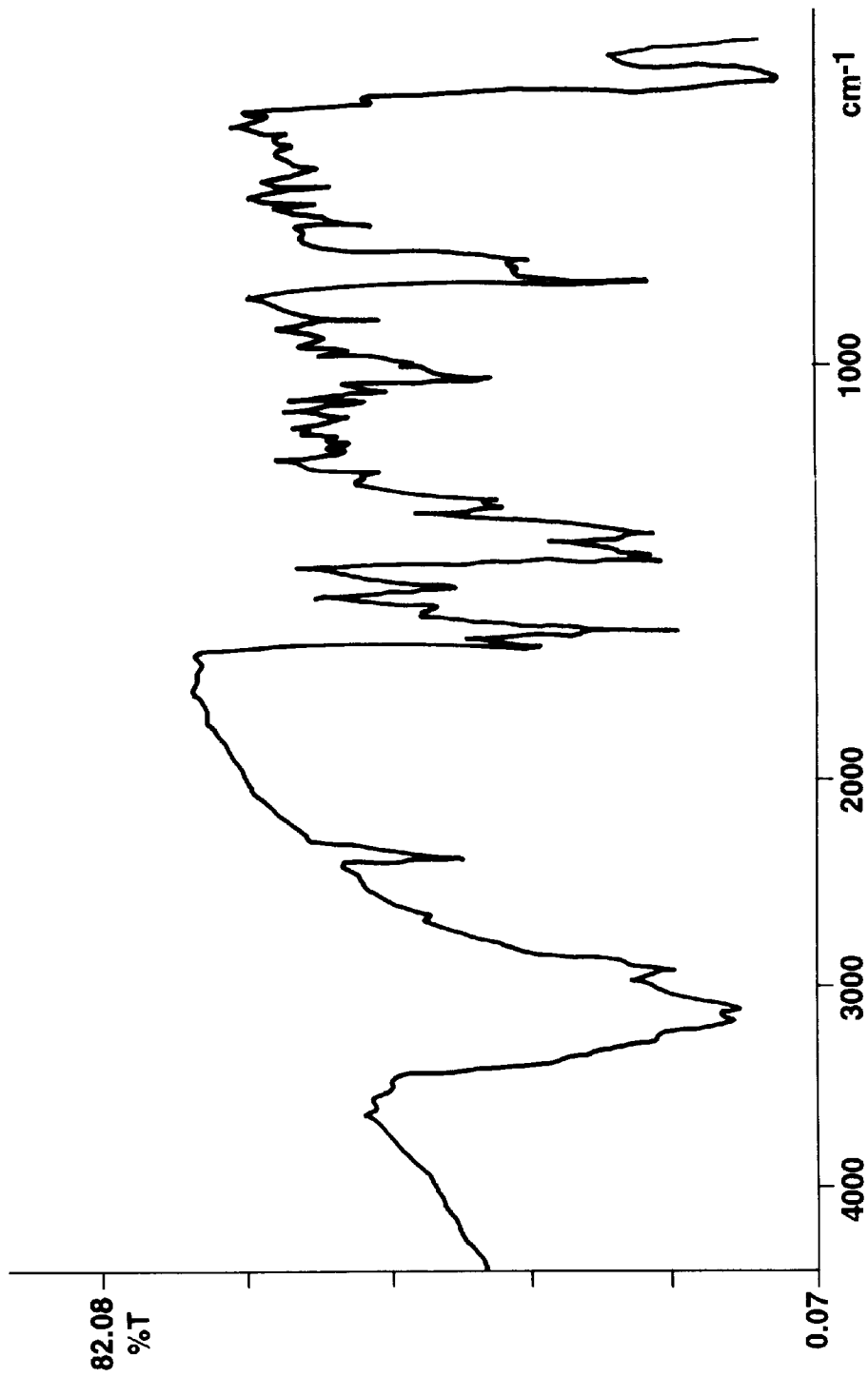
FIG. 1 is a view showing an infrared absorption spectrum of a pyrrole derivative according to the present invention, which was obtained in Example 6.

Next, the present invention is described in more detail by way of examples and comparative examples. However, these examples are not intended to limit the scope of the present invention, and various modifications and changes can be made thereto unless they departs from the scope of the present invention.

CATALYST PRODUCTION EXAMPLE 1

Tin tetrachloride (108.2 mg, 0.415 mmol) was added to a toluene solution (2 ml) containing 2,5-dimethyl pyrrole (59.29 mg, 0.623 mmol) at room temperature under a nitrogen atmosphere to produce a suspension containing a yellow precipitate. After the suspension was stirred for 15 minutes, a toluene solution (3.1 ml) containing of triethyl aluminum (357.9 mg, 3.12 mmol) was added thereto and reacted with each other for 15 minutes. A toluene solution (2 ml) containing chromium(III)-2-ethyl hexanoate (100 mg, 0.204 mmol) was added to the obtained solution and reacted with each other for 15 minutes. Thereafter, toluene was removed by distillation from the reaction solution at room temperature under a reduced pressure. The resultant brown oil was diluted with cyclohexane (10 ml) to obtain a catalyst suspension (10.5 ml).

CATALYST PRODUCTION EXAMPLE 2

The same procedure as in Catalyst Production Example 1 was conducted except that a toluene solution (10 ml) containing 2,5-dimethyl pyrrole (59.29 mg, 0.623 mmol) was used instead of the toluene solution (2 ml) containing 2,5-dimethyl pyrrole (59.29 mg, 0.623 mmol), to obtain a catalyst suspension.

CATALYST PRODUCTION EXAMPLE 3

Carbon tetrachloride (31.95 mg, 0.208 mmol) was added to a toluene solution (5 ml) containing 2,5-dimethyl pyrrole (29.59 mg, 0.311 mmol) at room temperature under a nitrogen atmosphere. A toluene solution (1.55 ml) containing triethyl aluminum (177.8 mg, 1.55 mmol) was added to the obtained solution and reacted with each other for 30 minutes. A toluene solution (1 ml) containing chromium (III)-2-ethyl hexanoate (50 mg, 0.102 mmol) was added to the obtained solution and reacted with each other for 15 minutes. Thereafter, toluene was removed by distillation from the reaction solution at room temperature under a reduced pressure. The resultant brown oil was diluted with cyclohexane (5 ml) to obtain a catalyst solution (5.2 ml).

CATALYST PRODUCTION EXAMPLE 4

2,5-Dimethyl pyrrole (59.29 mg, 0.623 mmol) and tin tetrachloride (108.2 mg, 0.415 mmol) were in turn added to a toluene solution (4 ml) containing chromium(III)-2-ethyl hexanoate (100 mg, 0.204 mmol) at room temperature under a nitrogen atmosphere and reacted with each other at room temperature for one hour. A toluene solution (3.1 ml) containing triethyl aluminum (357.9 ml, 3.12 mmol) was gradually dropped into the obtained green suspension and reacted with each other for 15 minutes. Thereafter, toluene was removed by distillation from the reaction solution at room temperature under a reduced pressure. The resultant deep brown oil was diluted with cyclohexane (10 ml) to obtain a catalyst suspension (10.5 ml).

CATALYST PRODUCTION EXAMPLE 5

The same procedure as in Catalyst Production Example 4 was conducted except that a toluene solution (12 ml) containing of chromium(III)-2-ethyl hexanoate (100 mg, 0.204 mmol) was used instead of the toluene solution (4 ml) containing chromium(III)-2-ethyl hexanoate (100 mg, 0.204 mmol), to obtain a catalyst suspension.

CATALYST PRODUCTION EXAMPLE 6

2,5-dimethyl pyrrole (59.29 mg, 0.623 mmol) and carbon tetrachloride (63.89 mg, 0.415 mmol) were in turn added to a toluene solution (12 ml) containing chromium(III)-2-ethyl hexanoate (100 mg, 0.204 mmol) at room temperature under a nitrogen atmosphere and reacted with each other at room temperature for one hour. A toluene solution (3.1 ml) containing triethyl aluminum (357.9 ml, 3.12 mmol) was gradually dropped into the obtained green solution and reacted with each other for 15 minutes. Thereafter, toluene was removed by distillation from the reaction solution at room temperature under a reduced pressure. The resultant brown oil was diluted with cyclohexane (10 ml) to obtain a catalyst solution (10.5 ml).

EXAMPLE 1

A 300 milliliter-autoclave was dried at 150° C. in a dryer, and assembled while maintained in a hot state. Thereafter, the content of the autoclave was vacuum-evacuated and replaced with a nitrogen gas. Cyclohexane (100 ml) and the catalyst suspension (0.47 ml) produced in Catalyst Production Example 1 were charged into the autoclave at room temperature under a nitrogen atmosphere. While heating the autoclave at 80° C., ethylene was introduced thereinto until the total pressure of ethylene within the autoclave reached 38 kg/cm². Thereafter, the total pressure of ethylene and the reaction temperature within the autoclave were maintained at 38 kg/cm² and 80° C., respectively. After 30 minutes, ethanol was introduced under pressure into the autoclave to terminate the reaction.

The results of composition analysis of the reaction product by gas chromatography, and the like are shown in Table 1. It was confirmed that the total amount of the reaction product produced was 11.33 g and the catalytic activity (g-α-olefin/g-Cr·Hr) was 47518. Further, it was confirmed that the reaction product was composed mainly of 1-hexene and the purity of 1-hexene was 99.9% based on the obtained hexenes.

EXAMPLE 2

The same procedure as in Example 1 was conducted except that cyclohexane (125 ml) and the catalyst suspension (0.68 ml) produced in Catalyst Production Example 2 were charged into the autoclave. The results of composition analysis of the reaction product by gas chromatography, and the like are shown in Table 1. It was confirmed that the total amount of the reaction product produced was 32.63 g and the catalytic activity was 94725. Further, it was confirmed that the reaction product was composed mainly of 1-hexene and the purity of 1-hexene was 99.6% based on the obtained hexenes.

EXAMPLE 3

The same procedure as in Example 1 was conducted except that cyclohexane (125 ml) and the catalyst solution (0.68 ml) produced in Catalyst Production Example 3 were charged into the autoclave. The results of composition analysis of the reaction product by gas chromatography, and the like are shown in Table 1. It was confirmed that the total amount of the reaction product produced was 27.57 g and the catalytic activity was 80033. Further, it was confirmed that the reaction product was composed mainly of 1-hexene and the purity of 1-hexene was 99.7% based on the obtained hexenes.

COMPARATIVE EXAMPLE 1

The same procedure as in Example 1 was conducted except that cyclohexane (125 ml) and the catalyst suspension (0.68 ml) produced in Catalyst Production Example 4 were charged into the autoclave. The results of composition analysis of the reaction product by gas chromatography, and the like are shown in Table 2. It was confirmed that the total amount of the reaction product produced was 7.54 g and the catalytic activity was 21895. Further, it was confirmed that the reaction product was composed mainly of 1-hexene and the purity of 1-hexene was 99.9% based on the obtained hexenes.

COMPARATIVE EXAMPLE 2

The same procedure as in Example 1 was conducted except that cyclohexane (125 ml) and the catalyst suspension (0.68 ml) produced in Catalyst Production Example 5 were charged into the autoclave. The results of composition analysis of the reaction product by gas chromatography, and the like are shown in Table 2. It was confirmed that the total amount of the reaction product produced was 13.90 g and the catalytic activity was 40360. Further, it was confirmed that the reaction product was composed mainly of 1-hexene and the purity of 1-hexene was 99.6% based on the obtained hexenes.

COMPARATIVE EXAMPLE 3

The same procedure as in Example 1 was conducted except that cyclohexane (125 ml) and the catalyst suspension (0.68 ml) produced in Catalyst Production Example 6 were charged into the autoclave. The results of composition analysis of the reaction product by gas chromatography, and the like are shown in Table 2. It was confirmed that the total amount of the reaction product produced was 9.48 g and the catalytic activity was 27525. Further, it was confirmed that the reaction product was composed mainly of 1-hexene and the purity of 1-hexene was 99.7% based on the obtained hexenes.

In Tables 1 and 2, component-contacting methods indicated by symbols A and B in "Conditions for production of Cr-based catalyst" are as follows:

A: Method of adding the chromium compound to the mixed solution of the pyrrole ring-containing compound, the halogen-containing compound and the alkyl aluminum compound; and B: Method of adding, in turn, the chromium compound, the pyrrole ring-containing compound, the halogen-containing compound and the alkyl aluminum compound to the solvent.

In addition, in Tables 1 and 2, "CHX" in "Kind of solvent used for oligomerization" represents cyclohexane, and the units of the catalytic efficiency and the catalytic activity are "g-α-olefin/g-Cr compound" and "g-α-olefin/1 g-Cr·Hr", respectively.

TABLE 1

| Example No. | Example 1 | Example 2 | Example 3 |
|---|---|---|---|
| <Conditions for production of Cr-based catalyst> | | | |
| Concentration of Cr upon catalyst production (mmol/L) | 29 | 13 | 13 |
| Component-contacting method upon catalyst production | A | A | A |
| <Conditions for oligomerization> | | | |
| Catalyst Production Example No. of Cr-based catalyst used | 1 | 2 | 3 |
| Kind (amount: ml) of solvent used for oligomerization | CHX(100) | CHX(125) | CHX(125) |
| Atomic weight (mg) of Cr charged | 0.48 | 0.69 | 0.71 |
| Reaction temperature (° C.) | 80 | 80 | 80 |
| Ethylene pressure (kg/cm$^2$) | 38 | 38 | 38 |
| Reaction time (Hr) | 0.5 | 0.5 | 0.5 |
| <Total amount of reaction product (g)> | 11.33 | 32.63 | 27.57 |
| <Composition of reaction product (wt. %)> | | | |
| C4 | 0 | 0.05 | 0.07 |
| Total amount of C6 | 98.2 | 96.8 | 97.3 |
| Amount of 1-hexene in C6 (wt. %) | 99.9 | 99.6 | 99.7 |
| C8 | 0.6 | 0.5 | 0.6 |
| C10–C20 | 1.1 | 2.6 | 2.0 |
| C22–C30 | 0 | 0 | 0 |
| Wax | 0 | 0 | 0 |
| By-product polyethylene | 0.04 | 0.02 | 0.02 |
| <Catalytic efficiency> | 2518 | 5020 | 4242 |
| <Catalytic activity> | 47518 | 94725 | 80033 |

TABLE 2

| Comparative Example No. | Comparative Example 1 | Comparative Example 2 | Comparative Example 3 |
|---|---|---|---|
| <Conditions for production of Cr-based catalyst> | | | |
| Concentration of Cr upon catalyst production (mmol/L) | 29 | 13 | 13 |
| Component-contacting method upon catalyst production | B | B | B |
| <Conditions for oligomerization> | | | |
| Catalyst Production Example No. of Cr-based catalyst used | 4 | 5 | 6 |
| Kind (amount: ml) of solvent used for oligomerization | CHX(125) | CHX(125) | CHX(125) |
| Atomic weight (mg) of Cr charged | 0.69 | 0.69 | 0.70 |
| Reaction temperature (° C.) | 80 | 80 | 80 |
| Ethylene pressure (kg/cm$^2$) | 38 | 38 | 38 |
| Reaction time (Hr) | 0.5 | 0.5 | 0.5 |
| <Total amount of reaction product (g)> | 7.54 | 13.90 | 9.48 |
| <Composition of reaction product (wt. %)> | | | |
| C4 | 0.2 | 0.1 | 0.11 |
| Total amount of C6 | 98.1 | 97.6 | 97.9 |
| Amount of 1-hexene in C6 (wt. %) | 99.9 | 99.6 | 99.7 |
| C8 | 0.9 | 0.6 | 0.7 |
| C10–C20 | 0.8 | 1.6 | 1.2 |
| C22–C30 | 0 | 0 | 0 |
| Wax | 0 | 0 | 0 |
| By-product polyethylene | 0.05 | 0.09 | 0.05 |
| <Catalytic efficiency> | 1160 | 2139 | 1459 |
| <Catalytic activity> | 21895 | 40360 | 27525 |

CATALYST PRODUCTION EXAMPLE 7

2,5-dimethyl pyrrole (59.29 mg, 0.623 mmol) and tin tetrachloride (108.2 mg, 0.415 mmol) were in turn added to a toluene solution (22 ml) containing chromium(III)-2-ethyl hexanoate (100 mg, 0.204 mmol) at room temperature under a nitrogen atmosphere and reacted with each other at room temperature for one hour to produce a suspension containing a yellow precipitate. A toluene solution (3.1 ml) containing triethyl aluminum (449.27 mg, 3.12 mmol) was gradually dropped into the thus-produced suspension. The concentration of chromium in the reaction solution was 8 mmol/liter. After the reaction was continued for 15 minutes, toluene was removed by distillation from the reaction solution at room temperature under a reduced pressure. The resultant deep brown oil was diluted with cyclohexane to obtain a catalyst suspension (10.5 ml).

CATALYST PRODUCTION EXAMPLE 8

The same procedure as in Catalyst Production Example 7 was conducted except that a toluene solution (4 ml) containing chromium(III)-2-ethyl hexanoate (100 mg, 0.204 mmol) was used instead of the toluene solution (22 ml) containing chromium(III)-2-ethyl hexanoate (100 mg, 0.204 mmol), to obtain a catalyst suspension. Incidentally, the concentration of chromium in the reaction solution was 29 mmol/liter.

CATALYST PRODUCTION EXAMPLE 9

The procedure of Catalyst Production Example 7 was followed except that 12 ml of a toluene solution containing 100 mg (0.204 mmol) of chromium(III)-2-ethyl hexanoate was used instead of 22 ml of the toluene solution containing 100 mg (0.204 mmol) of chromium(III)-2-ethyl hexanoate, to obtain a catalyst suspension. Incidentally, the concentration of chromium in the reaction solution was 13 mmol/liter.

CATALYST PRODUCTION EXAMPLE 10

2,5-dimethyl pyrrole (118.57 mg, 1.246 mmol) and tin tetrachloride (215.9 mg, 0.829 mmol) were in turn added to a toluene solution (9 ml) containing chromium(III)-2-ethyl hexanoate (200 mg, 0.408 mmol) at room temperature under a nitrogen atmosphere. Before any precipitate was formed, a toluene solution (6.2 ml) containing triethyl aluminum (898.54 mg, 6.24 mmol) was gradually dropped into the reaction solution. The concentration of chromium in the reaction solution was 27 mmol/liter. After the reaction was continued for 15 minutes, toluene was removed by distillation from the reaction solution at room temperature under a reduced pressure. The resultant deep brown oil was diluted with cyclohexane to obtain a catalyst suspension (20 ml).

CATALYST PRODUCTION EXAMPLE 11

A mixed toluene solution (3.95 ml) containing ethyl aluminum chloride (107.91 mg, 0.85 mmol) and triethyl aluminum (449.27 mg, 3.12 mmol) was gradually dropped into a mixed toluene solution (2 ml) containing chromium (III)-2 -ethyl hexanoate (100 mg, 0.204 mmol) and 2,5-dimethyl pyrrole (59.29 mg, 0.623 mmol) at room temperature under a nitrogen atmosphere. The concentration of chromium in the reaction solution was 34.3 mmol/liter. After the reaction was continued for 15 minutes, toluene was removed by distillation from the reaction solution at room temperature under a reduced pressure. The resultant deep brown oil was diluted with cyclohexane to obtain a catalyst suspension (11 ml).

EXAMPLE 4

A 300 milliliter-autoclave was dried at 150° C. in a dryer, and assembled while maintained in a hot state. Thereafter, the content of the autoclave was vacuum-evacuated and replaced with a nitrogen gas. Cyclohexane (125 ml) and the catalyst suspension (0.68 ml) produced in Catalyst Production Example 7 wee charged into the autoclave at room temperature under a nitrogen atmosphere. After the autoclave was heated to 80° C., ethylene was introduced thereinto until the total pressure of ethylene within the autoclave reached 38 kg/cm$^2$. Thereafter, the total pressure of ethylene and the reaction temperature within the autoclave were maintained at 38 kg/cm$^2$ and 80° C., respectively. After 30 minutes, ethanol was introduced under pressure into the autoclave to terminate the reaction.

The results of composition analysis of the reaction product by gas chromatography, and the like are shown in Table 3. It was confirmed that the total amount of the reaction product was 17.67 g and the catalytic activity (g-α-olefin/ g-Cr·Hr) was 51295. Further, it was confirmed that the reaction product was composed mainly of 1-hexene and the purity of 1-hexene was 99.7% based on the obtained hexenes.

EXAMPLE 5

The autoclave was conditioned in the same manner as in Example 4, and charged with, in turn, cyclohexane (120 ml), a heptane solution containing 2,5-dimethyl pyrrole (7.41 mg, 0.078 mmol), a heptane solution containing a germanium tetrachloride (11.13 mg, 0.052 mmol), a heptane solution containing triethyl aluminum (44.7 mg, 0.39 mmol) and a heptane solution containing chromium(III)-2-ethyl hexanoate (12.5 mg, 0.025 mmol). After the autoclave was heated to 80° C., ethylene was introduced thereinto until the total pressure of ethylene within the autoclave reached 38 kg/cm$^2$. The concentration of chromium in the reaction solution was 0.2 mmol/liter. Thereafter, ethylene was introduced to the autoclave and reacted therein in the same manner as in Example 4 except that the ethylene pressure during the reaction was changed to 35 kg/cm$^2$.

The results of composition analysis of the reaction product by gas chromatography, and the like are shown in Table 3. It was confirmed that the total amount of the reaction product was 62.31 g and the catalytic activity was 94047. Further, it was confirmed that the reaction product was composed mainly of 1-hexene and the purity of 1-hexene was 99.2% based on the obtained hexenes.

COMPARATIVE EXAMPLE 4

The same procedure as in Example 4 was conducted except that the catalyst suspension (0.68 ml) produced in Catalyst Production Example 8 was charged into the autoclave instead of the catalyst suspension produced in Catalyst Production Example 7. The results of composition analysis of the reaction product by gas chromatography, and the like are shown in Table 3. It was confirmed that the total amount of the reaction product was 7.54 g and the catalytic activity was 21895. Further, it was confirmed that the reaction product was composed mainly of 1-hexene and the purity of 1-hexene was 99.9% based on the obtained hexenes.

COMPARATIVE EXAMPLE 5

The same procedure as in Example 4 was conducted except that 0.68 ml of the catalyst suspension produced in Catalyst Production Example 9 was charged into the autoclave instead of the catalyst suspension produced in Catalyst Production Example 7. The results of composition analysis of the reaction product by gas chromatography, and the like are shown in Table 4. It was confirmed that the total amount of the reaction product was 13.90 g and the catalytic activity was 40360. Further, it was confirmed that the reaction product was composed mainly of 1-hexene and the purity of 1-hexene was 99.6% based on the obtained hexenes.

COMPARATIVE EXAMPLE 6

The procedure of Example 4 was followed except that the catalyst suspension (1 ml) produced in Catalyst Production Example 10 was charged into the autoclave instead of the catalyst suspension produced in Catalyst Production Example 7. The results of composition analysis of the reaction product by gas chromatography, and the like are shown in Table 4. It was confirmed that the total amount of the reaction product was 1.24 g and the catalytic activity was 2342. Further, it was confirmed that the reaction product was composed mainly of 1-hexene and the purity of 1-hexene was 99.6% based on the obtained hexenes.

COMPARATIVE EXAMPLE 7

The same procedure as in Example 4 was conducted except that the catalyst suspension (0.5 ml) produced in Catalyst Production Example 11 and cyclohexane (100 ml) were charged into the autoclave instead of the catalyst suspension produced in Catalyst Production Example 7. The results of composition analysis of the reaction product by gas chromatography, and the like are shown in Table 4. It was confirmed that the total amount of the reaction product was 8.77 g and the catalytic activity was 36762. Further, it was confirmed that the reaction product was composed mainly of 1-hexene and the purity of 1-hexene was 99.7% based on the obtained hexenes.

In Tables 3 and 4, component-contacting methods indicated by symbols A, B and C in "Conditions for production of Cr-based catalyst" are as follows:

A: Method of adding the alkyl aluminum compound to the mixed suspension or solution of the chromium compound, the pyrrole ring-containing compound and the halogen-containing compound;

B: Method of adding the chromium compound to the mixed solution of the pyrrole ring-containing compound, the alkyl aluminum compound and the halogen-containing compound; and C: Method of adding the mixed solution of the alkyl aluminum compound and the halogen-containing compound to the mixed solution of the chromium compound and the pyrrole ring-containing compound.

In addition, in Tables 1 and 2, "CHX" and "HPT" in the "Kind of solvent used for oligomerization" represent cyclohexane and n-heptane, respectively, and units of the catalytic efficiency and the catalytic activity are "g-α-olefin/g-Cr compound" and "g-α-olefin/1 g-Cr·Hr", respectively.

TABLE 3

| Example No. and Comparative Example No. | Example 4 | Example 5 | Comparative Example 4 |
|---|---|---|---|
| <Conditions for production of Cr-based catalyst> | | | |
| Concentration of Cr upon catalyst production (mmol/L) | 8 | 0.2 | 29 |
| Component-contacting method upon catalyst production | A | B | A |
| <Conditions for oligomerization> | | | |
| Catalyst Production Example No. of Cr-based catalyst used | 7 | — | 8 |
| Kind (amount: ml) of solvent used for oligomerization | CHX(125) | CHX(120)/HPT(5) | CHX(125) |
| Atomic weight (mg) of Cr charged | 0.69 | 0.69 | 0.69 |
| Reaction temperature (° C.) | 80 | 80 | 80 |
| Ethylene pressure (kg/cm$^2$) | 38 | 35 | 38 |
| Reaction time (Hr) | 0.5 | 0.5 | 0.5 |
| <Total amount of reaction product (g)> | 17.67 | 62.31 | 7.54 |
| <Composition of reaction product (wt. %)> | | | |
| C4 | 0.08 | 0.02 | 0.2 |
| Total amount of C6 | 97.5 | 92.5 | 98.1 |
| Amount of 1-hexene in C6 (wt. %) | 99.7 | 99.2 | 99.9 |
| C8 | 0.6 | 0.4 | 0.9 |
| C10–C20 | 1.8 | 7.1 | 0.8 |
| C22–C30 | 0 | 0 | 0 |
| Wax | 0 | 0 | 0 |
| By-product polyethylene | 0.05 | 0.03 | 0.05 |
| <Catalytic efficiency> | 2719 | 4984 | 1160 |
| <Catalytic activity> | 51295 | 94047 | 21895 |

TABLE 4

| Comparative Example No. | Comparative Example 5 | Comparative Example 6 | Comparative Example 7 |
|---|---|---|---|
| <Conditions for production of Cr-based catalyst> | | | |
| Concentration of Cr upon catalyst production (mmol/L) | 13 | 27 | 34.3 |
| Component-contacting method upon catalyst production | A | A | C |
| <Conditions for oligomerization> | | | |
| Catalyst Production Example No. of Cr-based catalyst used | 9 | 10 | 11 |
| Kind (amount: ml) of solvent used | CHX(125) | CHX(125) | CHX(100) |
| Atomic weight (mg) of Cr charged | 0.69 | 1.08 | 0.48 |
| Reaction temperature (° C.) | 80 | 80 | 90 |
| Ethylene pressure (kg/cm$^2$) | 38 | 38 | 48 |
| Reaction time (Hr) | 0.5 | 0.5 | 0.5 |
| <Total amount of reaction product (g)> | 13.90 | 1.24 | 8.77 |
| <Composition of reaction product (wt. %)> | | | |
| C4 | 0.1 | 0.02 | 0.08 |
| Total amount of C6 | 97.6 | 98.9 | 98.1 |
| Amount of 1-hexene in C6 (wt. %) | 99.6 | 99.6 | 99.7 |
| C8 | 0.6 | 0.5 | 0.6 |
| C10–C20 | 1.6 | 0.2 | 1.2 |
| C22–C30 | 0 | 0 | 0 |
| Wax | 0 | 0 | 0 |
| By-product polyethylene | 0.09 | 0.04 | 0.05 |
| <Catalytic efficiency> | 2139 | 124 | 1948 |
| <Catalytic activity> | 40360 | 2342 | 36762 |

EXAMPLE 6

(Synthesis of Pyrrole Derivative)

2,5-dimethyl pyrrole (59.29 mg, 0.623 mmol) and tin tetrachloride (108.2 mg, 0.415 mmol) were reacted with each other in n-heptane (5 ml) at room temperature in a nitrogen atmosphere for 15 minutes to obtain a suspension containing a yellow precipitate. After filtering, the yellow precipitate was dried. The yield of the dried product was 131 mg. The yellow precipitate was subjected to structural analysis, so that it was confirmed that the product was a pyrrole derivative represented by the following general formula:

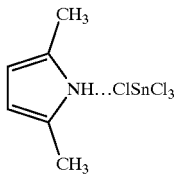

In addition, as seen in FIG. 1, the infrared absorption spectrum of the pyrrole derivative showed typical broad infrared absorption due to stretching vibration of hydrogen-bonded NH at a wavelength of 3100 to 3300 cm$^{-1}$.

Incidentally, it was confirmed that the yellow precipitate obtained in Catalyst Production Example 1 by adding, in turn, 2,5-dimethyl pyrrole and tin tetrachloride to the toluene solution containing chromium(III)-2-ethyl hexanoate and reacting these components with each other at room temperature for one hour, had the same infrared absorption spectrum as that of the afore-mentioned pyrrole derivative.

EXAMPLE 7

1) Production of Catalyst:

Tin tetrachloride (54.1 mg, 0.208 mmol) was added to a toluene solution (13.5 ml) containing 2,5-dimethyl pyrrole (29.65 mg, 0.312 mmol) at room temperature in a nitrogen atmosphere to obtain a suspension containing a yellow precipitate. After the thus-produced suspension was stirred for 15 minutes, a toluene solution (1.6 ml) containing triethyl aluminum (178.9 mg, 1.56 mmol) was added thereto, and the mixture was further stirred for 15 minutes. Added to the obtained solution was 1 ml of a toluene solution containing chromium(III)-2-ethyl hexanoate (50 mg, 0.104 mmol), and then the mixed solution was stirred for 15 minutes to produce a catalyst solution A.

2) Reaction Using the Catalyst Just Produced:

A 300 milliliter-autoclave was dried at 150° C. in a dryer, and assembled while maintained in a hot state. Thereafter, the content of the autoclave was vacuum-evacuated and replaced with a nitrogen gas. Cyclohexane (69 ml) and the catalyst solution A (1.0 ml) just produced were charged into the autoclave at room temperature under a nitrogen atmosphere. After the autoclave was heated to 140° C., ethylene was introduced thereinto until the total pressure of ethylene in the autoclave reached 48 kg/cm$^2$ G. Thereafter, the total pressure of ethylene and the reaction temperature within the autoclave were maintained at 48 kg/cm$^2$ G and 140° C., respectively.

After the reaction was continued for 30 minutes, ethanol was introduced under pressure into the autoclave to terminate the reaction. The results are shown in Table 5.

3) Reaction Using the Catalyst Preserved in Toluene:

The catalyst solution A was preserved at room temperature under a nitrogen atmosphere for 5 days to obtain a catalyst solution B. The procedure of the afore-mentioned item 2) was followed except that the catalyst solution B was used, to conduct the oligomerization of ethylene. As a result, it was confirmed that the catalyst solution B still maintained a catalytic activity corresponding to 84% of the catalytic activity of the catalyst solution A just produced. The results are shown in Table 5.

EXAMPLES 8

1) Production of Catalyst:

Tin tetrachloride (108.2 mg, 0.415 mmol) was added to a toluene solution (10 ml) containing 2,5-dimethyl pyrrole (59.29 mg, 0.623 mmol) at room temperature under a nitrogen atmosphere to produce a suspension containing a yellow precipitate. After the thus-produced suspension was stirred for 15 minutes, a toluene solution (3.1 ml) containing triethyl aluminum (357.9 mg, 3.12 mmol) was added thereto, and the mixture was further stirred for 15 minutes. Added to the obtained solution was a toluene solution (2 ml) containing chromium(III)-2-ethyl hexanoate (100 mg, 0.204 mmol). After the mixed solution was further stirred for 15 minutes, toluene was removed by distillation from the mixed solution. Cyclohexane (10 ml) was added to the obtained brown oily substance to produce a catalyst suspension C (10.5 ml).

2) Reaction Using the Catalyst Just Produced:

A 300 milliliter-autoclave was dried at 150° C. in a dryer, and assembled while maintained in a hot state. Thereafter, the content of the autoclave was vacuum-evacuated and replaced with a nitrogen gas. Cyclohexane (125 ml) and the catalyst suspension C (0.68 ml) just produced were charged into the autoclave at room temperature under a nitrogen atmosphere. After the autoclave was heated to 80° C., ethylene was introduced thereinto until the total pressure of ethylene in the autoclave reached 38 kg/cm$^2$ G. Thereafter, the total pressure of ethylene and the reaction temperature within the autoclave were maintained at 38 kg/cm$^2$ G and 80° C., respectively.

After the reaction was continued for 30 minutes, ethanol was introduced under pressure into the autoclave to terminate the reaction. The results are shown in Table 6.

3) Reaction Using the Catalyst Preserved in Cyclohexane:

The catalyst suspension C was preserved at room temperature under a nitrogen atmosphere for 5 days to obtain a catalyst suspension D. The procedure as defined above was followed except that the catalyst suspension D was used, to conduct the oligomerization of ethylene. As a result, it was confirmed that in the case where the catalyst thus preserved in the absence of the unsaturated hydrocarbon was used, the catalytic activity thereof was 39% of the catalytic activity of the catalyst suspension C just produced. The results are shown in Table 6.

REFERENCE EXAMPLES 1

1) Production of Catalyst:

A toluene solution (3.95 ml) containing ethyl aluminum dichloride (107.91 mg, 0.85 mmol) and triethyl aluminum (449.27 mg, 3.12 mmol) was slowly dropped into a toluene solution (2 ml) containing chromium(III)-2-ethyl hexanoate (100 mg, 0.204 mmol) and 2,5-dimethyl pyrrole (59.29 mg, 0.623 mmol) at room temperature under a nitrogen atmosphere. After the mixed solution was stirred for 15 minutes, toluene was removed by distillation therefrom under a reduced pressure. The obtained brown oily substance was diluted with cyclohexane to produce a catalyst suspension E (11.0 ml).

2) Reaction Using the Catalyst Just Produced:

A 300 milliliter-autoclave was dried at 150° C. in a dryer, and assembled while maintained in a hot state. Thereafter, the content of the autoclave was vacuum-evacuated and replaced with a nitrogen gas. Cyclohexane (100 ml), toluene (1.46 ml) and the catalyst suspension E (0.5 ml) just produced were charged into the autoclave at room temperature under a nitrogen atmosphere. After the autoclave was heated to 140° C., ethylene was introduced thereinto until the total pressure of ethylene in the autoclave reached 48 kg/cm$^2$ G. Thereafter, the total pressure of ethylene and the reaction temperature within the autoclave were maintained at 48 kg/cm$^2$ G and 140° C., respectively.

After the reaction was continued for 30 minutes, ethanol was introduced under pressure into the autoclave to terminate the reaction. The results are shown in Table 7.

3) Reaction Using the Catalyst Preserved in the Presence of Toluene:

Toluene (14.7 ml) was added to the catalyst suspension E just produced to obtain a catalyst suspension F. The catalyst suspension F was preserved at room temperature under a nitrogen atmosphere for 5 days.

The autoclave was assembled while maintained in a hot state, and vacuum-evacuated and replaced with a nitrogen gas in the same manner as defined in the above 2). After cyclohexane (100 ml) and the catalyst suspension F (1.96 ml) preserved for 5 days were charged into the autoclave, the oligomerization of ethylene was conducted at 48 kg/cm$^2$ G and 140° C. in the same manner as defined in the above 2). As a result, it was confirmed that the catalyst suspension F still maintained a catalytic activity corresponding to 84% of the catalytic activity of the catalyst suspension E just produced. The results are shown in Table 7.

4) Reaction Using the Catalyst Preserved in Cyclohexane:

Cyclohexane (14.7 ml) was added to the catalyst suspension E (5 ml) just produced to obtain a catalyst suspension G. The catalyst suspension G was preserved at room temperature under a nitrogen atmosphere for 5 days.

The autoclave was assembled while maintained in a hot state, and vacuum-evacuated and replaced with a nitrogen gas in the same manner as defined in the above 2). After cyclohexane (98.5 ml), toluene (1.46 ml) and the catalyst suspension G (1.96 ml) preserved for 5 days were charged into the autoclave, the oligomerization of ethylene was conducted at 48 kg/cm$^2$ G and 140° C. in the same manner as defined in the above 2). As a result, it was confirmed that the catalyst suspension G had a catalytic activity corresponding to 54% of the catalytic activity of the catalyst suspension F preserved in the presence of toluene. The results are shown in Table 7.

TABLE 5

|  | Catalyst solution A | Catalyst solution B |
|---|---|---|
| Total amount of reaction product (g) | 11.01 | 9.29 |
| Composition of reaction product (wt. %) | | |
| C4 | 0.01 | 0.01 |
| C6 | 96.9 | 97.3 |
| C6'*1 | 99.6 | 99.6 |
| C8 | 0.2 | 0.2 |
| C10–C20 | 2.8 | 2.4 |
| C22–C30 | 0 | 0 |
| Wax | 0 | 0 |
| By-product polyethylene | 0.06 | 0.09 |
| Catalytic activity*2 | 67038 | 56555 |

Note:
*1: Percentage of 1-hexene relative to total C6;
*2: unit: g-α-olefin/g-Cr · Hr

TABLE 6

|  | Catalyst solution C | Catalyst solution D |
|---|---|---|
| Total amount of reaction product (g) | 32.63 | 12.76 |
| Composition of reaction product (wt. %) | | |
| C4 | 0.05 | 0.06 |
| C6 | 96.8 | 97.3 |
| C6'*1 | 99.6 | 99.6 |
| C8 | 0.5 | 0.5 |
| C10–C20 | 2.6 | 2.0 |
| C22–C30 | 0 | 0 |
| Wax | 0 | 0 |
| By-product polyethylene | 0.02 | 0.05 |
| Catalytic activity*2 | 94725 | 37042 |

Note:
*1: Percentage of 1-hexene relative to total C6;
*2: unit: g-α-olefin/g-Cr · Hr

TABLE 7

|  | Catalyst solution E | Catalyst solution F | Catalyst solution G |
|---|---|---|---|
| Total amount of reaction product (g) | 5.70 | 4.76 | 2.59 |
| Composition of reaction product (wt. %) | | | |
| C4 | 0.02 | 0.02 | 0 |
| C6 | 98.1 | 98.3 | 98.5 |
| C6'*1 | 99.6 | 99.6 | 99.8 |
| C8 | 0.4 | 0.4 | 0.9 |
| C10–C20 | 1.4 | 1.2 | 0.6 |
| C22–C30 | 0 | 0 | 0 |
| Wax | 0 | 0 | 0 |
| By-product polyethylene | 0.05 | 0.06 | 0.06 |
| Catalytic activity*2 | 23912 | 19968 | 10865 |

Note:
*1: Percentage of 1-hexene relative to total C6;
*2: unit: g-α-olefin/g-Cr · Hr

EXAMPLE 9

1) Production of Catalyst:

Tin tetrachloride (54.1 mg, 0.208 mmol) was added to a toluene solution (5 ml) containing 2,5-dimethyl pyrrole (29.65 mg, 0.312 mmol) at room temperature under a nitrogen atmosphere to produce a suspension containing a yellow precipitate. After the thus-produced suspension was stirred for 15 minutes, a toluene solution (1.6 ml) containing triethyl aluminum (178.9 mg, 1.56 mmol) was added thereto, and the mixture was further stirred for 15 minutes. Added to the obtained solution was a toluene solution (1 ml) containing chromium(III)-2-ethyl hexanoate (50 mg, 0.104 mmol). After the mixed solution was further stirred for 15 minutes, toluene was removed by distillation from the mixed solution under a reduced pressure. The obtained brown oil was diluted with cyclohexane (5 ml) to obtain a catalyst suspension (5.2 ml).

2) Oligomerization of Ethylene:

A 300 milliliter-autoclave was dried at 150° C. in a dryer, and assembled while maintained in a hot state. Thereafter, the content of the autoclave was vacuum-evacuated and replaced with a nitrogen gas. Cyclohexane (80 ml) and the afore-mentioned catalyst suspension (0.44 ml) were charged into the autoclave at room temperature under a nitrogen atmosphere. After the autoclave was heated to 80° C., ethylene was introduced thereinto until the total pressure of ethylene in the autoclave reached 38 kg/cm$^2$ G. Thereafter, the total pressure of ethylene and the reaction temperature within the autoclave were maintained at 38 kg/cm$^2$ G and 80° C., respectively.

After the reaction was continued for 30 minutes, the reaction solution was sampled. Successively, an n-heptane solution (5 ml) containing carbon tetrachloride (2.61 mg, 0.017 mmol) and triethyl aluminum (14.91 mg, 0.13 mmol) was charged into the autoclave, and the reaction was continued therein for 30 minutes under the same condition as defined above. Thereafter, ethanol was introduced under pressure into the autoclave to terminate the reaction. The results are shown in Table 8.

EXAMPLE 10

Using the catalyst produced in Example 9, the same procedure as in Example 9 was conducted except that the additional amounts of halogen-containing compound and the alkyl aluminum compound was not supplied, to conduct the oligomerization of ethylene. The results are shown in Table 8.

TABLE 8

|  | Example 9 | | Example 10 | |
|---|---|---|---|---|
| Reaction time | 30 min. | 60 min. | 30 min. | 60 min. |
| Total amount of reaction product (g) | 16.19 | 47.18 | — | 21.07 |
| Composition of reaction product (wt. %) | | | | |
| C4 | 0.04 | 0.05 | — | 0.03 |
| C6 | 97.4 | 94.9 | — | 97.1 |
| C6'*1 | 99.8 | 99.7 | — | 99.8 |
| C8 | 0.5 | 0.4 | — | 0.5 |
| C10–C20 | 2.0 | 4.6 | — | 2.4 |
| C22–C30 | 0 | 0 | — | 0 |
| Wax | 0 | 0 | — | 0 |

TABLE 8-continued

|  | Example 9 |  | Example 10 |  |
|---|---|---|---|---|
| By-product polyethylene | 0.02 | 0.03 | — | 0.02 |
| Catalytic activity*[2] | 72726 | 105977 | — | 47320 |

Note:
*[1]: Percentage of 1-hexene relative to total C6;
*[2]: unit: g-α-olefin/g-Cr · Hr

INDUSTRIAL APPLICABILITY

In accordance with the present invention, there can be provided an industrially useful process capable of producing an α-olefin oligomer such as 1-hexene with extremely high yield and high selectivity.

What is claimed is:

1. A process for producing an α-oligomer, comprising the steps of:
   (1) preparing a reaction solution containing a chromium-based catalyst by bringing at least a chromium compound (a), a pyrrole ring-containing compound (b), an alkyl aluminum compound (c) and a halogen-containing compound (d) into contact with each other, wherein the chromium-based catalyst is prepared by bringing the pyrrole ring-containing compound (b), the alkyl aluminum compound (c) and the halogen-containing compound (d) into contact with each other in a hydrocarbon solvent, halogenated hydrocarbon solvent or mixture thereof, and then bringing the mixed resultant solution into contact with the chromium compound (a) and thereafter
   (2) contacting an α-olefin with the catalyst solution prepared in step (1) and oligomerizing the α-olefin.

2. A process according to claim 1, wherein the chromium-based catalyst is a catalyst prepared by bringing the pyrrole ring-containing compound (b), the alkyl aluminum compound (c) and the halogen-containing compound (d) into contact with each other in a hydrocarbon solvent, halogenated hydrocarbon solvent or mixture thereof in the absence of α-olefin, and then bringing the mixed resultant solution into contact with the chromium compound (a).

3. A process according to claim 1, wherein the concentration of the chromium compound (a) in the resultant mixed solution is $1 \times 10^{-7}$ to $3 \times 10^{-2}$ mol/liter.

4. A process according to claim 1, wherein the chromium-based catalyst is preserved in an organic solvent containing unsaturated hydrocarbon, when the chromium-based catalyst produced is stored for a long period of time before used in the oligomerization of α-olefin.

5. A process according to claim 4, wherein said chromium-based catalyst is preserved in an organic solvent containing unsaturated hydrocarbon in an amount of not less than 50 moles per mole of a chromium atom in the catalyst.

6. A process according to claim 4, wherein said chromium-based catalyst is preserved in an organic solvent containing unsaturated hydrocarbon in an amount of not less than 5% by weight.

7. A process according to claim 4, wherein said unsaturated hydrocarbon is an aromatic hydrocarbon having 6 to 12 carbon atoms.

8. A process according to claim 4, wherein said hydrocarbon solvent, halogenated hydrocarbon solvent or mixture thereof used for the production of the catalyst contains unsaturated hydrocarbon, and the chromium-based catalyst produced is preserved in the solvent as it is.

9. A process according to claim 1, wherein the oligomerization of α-olefin is conducted by a continuous method or by a semi-batch method, and an additional amount of the halogen-containing compound (d) is supplied in the course of the reaction.

10. A process according to claim 9, wherein the chromium-based catalyst is a catalyst prepared by bringing the chromium compound (a) or the alkyl aluminum compound (c) into contact with at least one of the pyrrole ring-containing compound (b) and the halogen-containing compound (d) with each other before bringing the chromium compound (a) and the alkyl aluminum compound (c) into contact with each other.

11. A process according to claim 9, wherein the oligomerization of α-olefin is conducted by a continuous method, and the additional amount of the halogen-containing compound (d) is supplied when the residence time of the catalyst in a reactor is not less than 5 minutes.

12. A process according to claim 9, wherein the oligomerization of α-olefin is conducted by a semi-batch method, and the additional amount of the halogen-containing compound (d) is supplied when the residence time of the catalyst in a reactor is not less than 5 minutes.

13. A process according to claim 9, wherein an additional amount of the alkyl aluminum compound (c) is supplied in addition to the additional amount of the halogen-containing compound (d).

14. A process according to claim 9, wherein the halogen-containing compound (d) additionally supplied contains a halogen atom bonded to an element belonging to 13-Group or 14-Group of the Periodic Table.

15. A process according to claim 1, wherein said chromium compound (a) is a salt of chromium and β-diketone, a salt of chromium and β-keto-carboxylic acid or a salt of chromium and other carboxylic acid.

16. A process according to claim 1, wherein the halogen-containing compound (d) contains an element selected from the group consisting of those belonging to 3-Group, 4-Group, 6-Group (exclusive of chromium), 13-Group, 14-Group and 15-Group of the Periodic Table.

17. A process according to claim 1, wherein said α-olefin subjected to the oligomerization is ethylene, and said α-olefin oligomer contains 1-hexene as a main component.

18. A process for producing an α-olefin oligomer, comprising the steps of:
   (1) preparing a reaction solution containing a chromium-based catalyst produced by bringing at least a chromium compound (a), a pyrrole ring-containing compound (b), an alkyl aluminum compound (c) and a halogen-containing compound (d) into contact with each other, wherein the chromium-based catalyst is prepared by bringing the chromium compound (a), the pyrrole ring-containing compound (b), the alkyl aluminum compound (c) and the halogen-containing compound (d) into contact with each other in a hydrocarbon solvent, halogenated hydrocarbon solvent or mixture thereof in the absence of α-olefin under such a condition that the concentration of the chromium compound (a) in the resultant mixed solution is adjusted to not more than $8 \times 10^{-3}$ mol/liter and thereafter,
   (2) contacting an α-olefin with the catalyst solution prepared in step (1) and oligomerizing the α-olefin.

19. A process according to claim 18, wherein the concentration of the chromium compound (a) in the resultant mixed solution is $1 \times 10^{-3}$ to $8 \times 10^{-3}$ mol/liter.

20. A process according to claim 18, wherein the chromium-based catalyst is a catalyst prepared by bringing the pyrrole ring-containing compound (b), the alkyl aluminum compound (c) and the halogen-containing compound (d) into contact with each other, and then bringing the mixed resultant solution into contact with the chromium compound (a).

21. A process according to claim 18, wherein the chromium-based catalyst is a catalyst prepared by first bringing the chromium compound (a), the pyrrole ring-containing compound (b) and the halogen-containing compound (d) into contact with each other in the solvent to produce a reaction product of the pyrrole ring-containing compound (b) and the halogen-containing compound (d) in the form of a precipitate, and then adding the alkyl aluminum compound (c) to the reaction mixture.

22. A process according to claim 21, wherein the main component of the precipitate is a pyrrole derivative represented by the general formula (I):

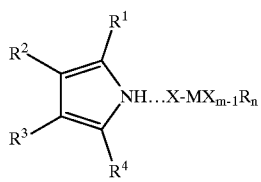

(I)

wherein $R^1$ to $R^4$ are a hydrogen atom or a linear or branched hydrocarbon group having 1 to 20 carbon atoms, in which $R^3$ and $R^4$ may integrally form a ring; X is a halogen atom; M is an element selected from the group consisting of those belonging to 3-Group, 4-Group, 6-Group (exclusive of chromium), 13-Group, 14-Group and 15-Group of the Periodic Table; m and n are numbers satisfying the relationships of $1 \leq m \leq 6$, $0 \leq n \leq 5$ and $2 \leq m+n \leq 6$ with the proviso that the sum of m and n is identical to the valence of the element M; n represents the number of Rs; and R is a hydrogen atom or a linear or branched hydrocarbon group having 1 to 20 carbon atoms and when n is not less than 2, Rs may be the same or different.

23. A process according to claim 18, wherein the chromium-based catalyst is a catalyst prepared by first bringing the pyrrole ring-containing compound (b) and the halogen-containing compound (d) into contact with each other in the solvent to produce a reaction product of the pyrrole ring-containing compound (b) and the halogen-containing compound (d) in the form of a precipitate, and then adding, in turn, the chromium compound (a) and the alkyl aluminum compound (c) to the reaction mixture.

24. A process according to claim 23, wherein the main component of the precipitate is a pyrrole derivative represented by the general formula (I):

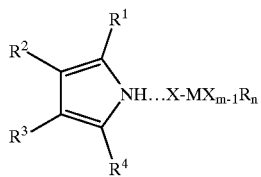

(I)

wherein $R^1$ to $R^4$ are a hydrogen atom or a linear or branched hydrocarbon group having 1 to 20 carbon atoms, in which $R^3$ and $R^4$ may integrally form a ring; X is a halogen atom; M is an element selected from the group consisting of those belonging to 3-Group, 4-Group, 6-Group (exclusive of chromium), 13-Group, 14-Group and 15-Group of the Periodic Table; m and n are numbers satisfying the relationships of $1 \leq m \leq 6$, $0 \leq n \leq 5$ and $2 \leq m+n \leq 6$ with the proviso that the sum of m and n is identical to the valence of the element M; n represents the number of Rs; and R is a hydrogen atom or a linear or branched hydrocarbon group having 1 to 20 carbon atoms and when n is not less than 2, Rs may be the same or different.

25. A process according to claim 18, wherein the chromium-based catalyst is a catalyst prepared by bringing a mixture obtained by preliminarily mixing the chromium compound (a) and the pyrrole ring-containing compound (b) together, into contact with a mixture obtained by preliminarily mixing the alkyl aluminum compound (c) and the halogen-containing compound (d) together.

26. A process according to claim 18, wherein the chromium-based catalyst is preserved in an organic solvent containing unsaturated hydrocarbon, when the chromium-based catalyst produced is stored for a long period of time before used in the oligomerization of α-olefin.

27. A process according to claim 18, wherein the oligomerization of α-olefin is conducted by a continuous method or by a semi-batch method, and an additional amount of the halogen-containing compound (d) is supplied in the course of the reaction.

28. A process according to claim 18, wherein said chromium compound (a) is a salt of chromium and β-diketone, a salt of chromium and β-keto-carboxylic acid or a salt of chromium and other carboxylic acid.

29. A process according to claim 18, wherein the halogen-containing compound (d) contains an element selected from the group consisting of those belonging to 3-Group, 4-Group, 6-Group (exclusive of chromium), 13-Group, 14-Group and 15-Group of the Periodic Table.

30. A process according to claim 18, wherein said α-olefin subjected to the oligomerization is ethylene, and said α-olefin oligomer contains 1-hexene as a main component.

31. A pyrrole derivative represented by the general formula (I):

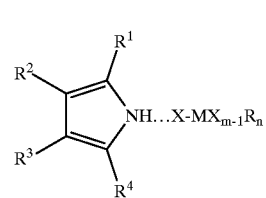

(I)

wherein $R^1$ to $R^4$ are a hydrogen atom or a linear or branched hydrocarbon group having 1 to 20 carbon atoms, in which $R^3$ and $R^4$ may integrally form a ring; X is a halogen atom; M is an element selected from the group consisting of those belonging to 3-Group, 4-Group, 6-Group (exclusive of chromium), 13-Group, 14-Group and 15-Group of the Periodic Table; m and n are numbers satisfying the relationships of $1 \leq m \leq 6$, $0 \leq n \leq 5$ and $2 \leq m+n \leq 6$ with the proviso that the sum of m and n is identical to the valence of the element M; n represents the number of Rs; and R is a hydrogen atom or a linear or branched hydrocarbon group having 1 to 20 carbon atoms and when n is not less than 2, Rs may be the same or different.

* * * * *